United States Patent
Zhu et al.

(10) Patent No.: US 12,138,306 B2
(45) Date of Patent: *Nov. 12, 2024

(54) FcRn-TARGETED MUCOSAL VACCINATION AGAINST RSV

(71) Applicant: University Of Maryland, College Park, MD (US)

(72) Inventors: Xiaoping Zhu, Clarksville, MD (US); Weizhong Li, College Park, MD (US)

(73) Assignee: University Of Maryland, College Park, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/831,928

(22) Filed: Jun. 3, 2022

(65) Prior Publication Data

US 2022/0401547 A1    Dec. 22, 2022

Related U.S. Application Data

(63) Continuation of application No. 16/117,915, filed on Aug. 30, 2018, now Pat. No. 11,376,317.

(60) Provisional application No. 62/552,041, filed on Aug. 30, 2017.

(51) Int. Cl.
| | |
|---|---|
| *A61K 39/12* | (2006.01) |
| *A61P 31/14* | (2006.01) |
| *C07K 14/005* | (2006.01) |
| *C07K 16/00* | (2006.01) |
| *A61K 9/00* | (2006.01) |
| *A61K 39/00* | (2006.01) |
| *C07K 14/00* | (2006.01) |

(52) U.S. Cl.
CPC .............. *A61K 39/12* (2013.01); *A61P 31/14* (2018.01); *C07K 14/005* (2013.01); *C07K 16/00* (2013.01); *A61K 9/0043* (2013.01); *A61K 2039/55561* (2013.01); *A61K 2039/55572* (2013.01); *C07K 14/00* (2013.01); *C07K 2317/52* (2013.01); *C07K 2319/30* (2013.01); *C12N 2760/18522* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | |
|---|---|---|---|
| 11,376,317 B2* | 7/2022 | Zhu ........................ | A61P 31/14 |
| 11,591,371 B2 | 2/2023 | Zhu | |
| 2007/0009523 A1 | 1/2007 | Presta | |
| 2011/0086058 A1 | 4/2011 | Jiang | |
| 2013/0164286 A1 | 6/2013 | Chou et al. | |
| 2015/0079121 A1 | 3/2015 | Weiner et al. | |
| 2015/0125473 A1 | 5/2015 | Burt et al. | |
| 2018/0244756 A1 | 8/2018 | Graham et al. | |
| 2019/0060440 A1 | 2/2019 | Zhu et al. | |
| 2019/0359655 A1 | 11/2019 | Zhu | |
| 2022/0401547 A1 | 12/2022 | Zhu | |

FOREIGN PATENT DOCUMENTS

| | | |
|---|---|---|
| WO | PCT/US2018/055896 | 10/2018 |
| WO | WO/2019/046859 A1 | 3/2019 |
| WO | WO-2019/046864 A1 | 3/2019 |

OTHER PUBLICATIONS

Lu et al., J Virology vol. 85, pp. 10542-10553 (Year: 2011).*
Shan et al. Communications Biology | (2021) 4:1048 | https://doi.org/10.1038/s42003-021-02565-5 | nature.com/commsbio (Year: 2021).*
U.S. Appl. No. 16/117,915, filed Aug. 30, 2018, Xiaoping Zhu.
U.S. Appl. No. 62/552,041, filed Aug. 30, 2017, Xiaoping Zhu.
Allie SR, Randall TD. Pulmonary immunity to viruses. Clin Sci (Lond). Jun. 30, 2017;131(14):1737-1762.
Berneman A, Belec L, Fischetti VA, Bouvet JP. 1998. The specificity patterns of human immunoglobulin G antibodies in serum differ from those in autologous secretions. Infect Immun. 66:4163-4168.
Boukhvalova MS, Blanco JC. 2013. The cotton rat Sigmodon hispidus model of respiratory syncytial virus infection. Curr Top Microbiol Immunol. 372:347-58.
Castilow EM, Varga SM. 2008. Overcoming T cell-mediated immunopathology to achieve safe RSV vaccination. Future Virol. 3:445-454.
Cullen LM, Blanco JC, Morrison TG. 2015. Cotton rat immune responses to virus-like particles containing the pre-fusion form of respiratory syncytial virus fusion protein. J Transl Med. 13:350.
Garg R, Latimer L, Simko E, Gerdts V, Potter A, van den Hurk Sv. Induction of mucosal immunity and protection by intranasal immunization with a respiratory syncytial virus subunit vaccine formulation. J Gen Virol. Feb. 2014;95(Pt 2):301-6.
Garg R, Theaker M, Martinez EC, van Drunen Littel-van den Hurk S. A single intranasal immunization with a subunit vaccine formulation induces higher mucosal IgA production than live respiratory syncytial virus. Virology. Dec. 2016;499:288-297.

(Continued)

*Primary Examiner* — Shanon A. Foley
*Assistant Examiner* — Myron G Hill
(74) *Attorney, Agent, or Firm* — Ballard Spahr LLP

(57) ABSTRACT

Disclosed are peptides comprising a monomeric Fc fragment of an immunoglobulin recognized by a neonatal receptor (FcRn); a modified pre-fusion respiratory syncytia virus (RSV) F protein; and a trimerization domain. Disclosed are nucleic acid sequences capable of encoding peptides comprising a monomeric Fc fragment of an immunoglobulin recognized by a neonatal receptor (FcRn); a modified pre-fusion respiratory syncytia virus (RSV) F protein; and a trimerization domain. Also disclosed are methods for eliciting a protective immune response against RSV comprising administering to a subject an effective amount of a composition comprising a monomeric Fc fragment of an immunoglobulin recognized by FcRn; a modified pre-fusion RSV F protein; and a trimerization domain, wherein the administering is to a mucosal epithelium.

23 Claims, 4 Drawing Sheets
Specification includes a Sequence Listing.

(56) References Cited

OTHER PUBLICATIONS

Gebril A, Alsaadi M, Acevedo R, Mullen AB, Ferro VA. 2012. Optimizing efficacy of mucosal vaccines. Expert Rev Vaccines. 11:1139-55.
Graham BS, Modjarrad K, McLellan JS. 2015. Novel antigens for RSV vaccines. Curr Opin Immunol. 35:30-8.
Holmgren J, Svennerholm AM. 2012. Vaccines against mucosal infections. Curr Opin Immunol. 24:343-53.
http://www.grandviewresearch.com/press-release/global-vaccine-market.
https://seekingalpha.com/article/4061495-novavax-will-ride-high-rsv-vaccine-wave-2017.
https://www.cdc.gov/features/rsv/.
https://www.fiercepharma.com/vaccines/bavarian-nordic-reports-positive-rsv-vaccine-top-line-phase-2-data.
https://www.fiercepharma.com/vaccines/novavax-still-gunning-for-first-to-market-status-rsv-ceo.
Johnson TR, Rangel D, Graham BS, Brough DE, Gall JG. Genetic vaccine for respiratory syncytial virus provides protection without disease potentiation. Mol Ther. Jan. 2014;22(1):196-205.
Johnson TR, Rao S, Seder RA, Chen M, Graham BS. 2009. TLR9 agonist, but not TLR7/8, functions as an adjuvant to diminish FI-RSV vaccine-enhanced disease, while either agonist used as therapy during primary RSV infection increases disease severity. Vaccine. 27:3045-52.
Joyce MG, et al. 2016. Iterative structure-based improvement of a fusion-glycoprotein vaccine against RSV. Nat Struct Mol Biol. 23:811-20.
Kinnear E, Lambert L, McDonald JU, Cheeseman HM, Caproni LJ, Tregoning JS. Airway T cells protect against RSV infection in the absence of antibody. Mucosal Immunol. May 24, 2017.
Krarup A, et al., 2015. A highly stable prefusion RSV F vaccine derived from structural analysis of the fusion mechanism. Nat Commun. 6:8143.
Liang et al., Enhanced Neutralizing Antibody Response Induced by Respiratory Syncytial Virus Prefusion F Protein Expressed by a Vaccine Candidate. J Virol. 2015, vol. 89(18), p. 9499-510.
Lu L, Palaniyandi S, Zeng R, Bai Y, Liu X, Wang Y, Pauza CD, Roopenian DC, Zhu X. 2011. An FcRn-targeted mucosal vaccine strategy effectively induces HIV-1 antigen-specific immunity to genital infection. J. Virol. 85:10542-10553.
McGhee JR. 2011. A mucosal gateway for vaccines. Nat Biotechnol. 29:136-8.
McLellan et al., Structure-Based Design of a Fusion Glycoprotein Vaccine for Respiratory Syncytial Virus. Science. 2013, vol. 342(6158).
McMaster SR, Wilson JJ, Wang H, Kohlmeier JE. 2015. Airway-Resident Memory CD8 T Cells Provide Antigen-Specific Protection against Respiratory Virus Challenge through Rapid IFN-? Production. J Immunol. 195:203-9.
Moghaddam A, Olszewska W, Wang B, Tregoning JS, Helson R, Sattentau QJ, Openshaw PJ. 2006. A potential molecular mechanism for hypersensitivity caused by formalin-inactivated vaccines. Nat Med. 12:905-7.
Morabito KM, Ruckwardt TR, Redwood AJ, Moin SM, Price DA, Graham BS. 2017. Intranasal administration of RSV antigen-expressing MCMV elicits robust tissue-resident effector and effector memory CD8+ T cells in the lung. Mucosal Immunol. 10:545-554.
Neutra MR, Kozlowski PA. 2006. Mucosal vaccines: the promise and the challenge. Nat Rev Immunol. 6:148-58.
Ngwuta JO, et al. 2015. Prefusion F-specific antibodies determine the magnitude of RSV neutralizing activity in human sera. Sci Transl Med. 7:309ra162.
Openshaw PJ, Tregoning JS. 2005. Immune responses and disease enhancement during respiratory syncytial virus infection. Clin Microbiol Rev. 18:541-55.
Oshansky CM, Zhang W, Moore E, Tripp RA. 2009. The host response and molecular pathogenesis associated with respiratory syncytial virus infection. Future Microbiol. 4:279-97.
Palomo C, et al. 2016. Influence of Respiratory Syncytial Virus F Glycoprotein Conformation on Induction of Protective Immune Responses. J Virol. 90:5485-98.
Passmore C, et al. Intranasal immunization with W 80 5EC adjuvanted recombinant RSV rF-ptn enhances clearance of respiratory syncytial virus in a mouse model. Hum Vaccin Immunother. 2014;10(3):615-22.
Pavot V, Rochereau N, Genin C, Verrier B, Paul S. 2012. New insights in mucosal vaccine development. Vaccine. 30:142-54.
Pierantoni A, et al. Mucosal delivery of a vectored RSV vaccine is safe and elicits protective immunity in rodents and nonhuman primates. Mol Ther Methods Clin Dev. May 20, 2015;2:15018.
Rath et al., Regulation of immune responses by the neonatal Fc receptor and its therapeutic implications. Front Immunol. 2015, vol. 5:664.
Roopenian DC, Akilesh S. 2007. FcRn: the neonatal Fc receptor comes of age. Nat Rev Immunol. 7:715-25.
Ruan et al., Suppressive effect of locally produced interleukin-10 on respiratory syncytial virus infection. Immunology. 2001, vol. 104(3), p. 355-60.
Vissers M, Ahout IML, de Jonge MI, Ferwerda G. 2016. Mucosal IgG levels correlate better with respiratory syncytial virus load and inflammation than plasma IgG levels. Clin Vaccine Immunol 23:243-245.
Yang K, Varga SM. 2014. Mucosal vaccines against respiratory syncytial virus. Curr Opin Virol. 6:78-84.
Ye L, Zeng R, Bai Y, Roopenian DC, Zhu X. 2011. Efficient mucosal vaccination mediated by the neonatal Fc receptor. Nature Biotechnol. 29:158-163.
International Search Report and Written Opinion were mailed on Feb. 22, 2019 by the International Searching Authority for International Application No. PCT/US2018/055896, filed on Oct. 15, 2018 and published as WO 2019/046864 on Apr. 4, 2019 (Applicant-Xiaoping Zhu) (14 Pages).
Afkhami, S. et al. Respiratory mucosal delivery of next-generation COVID-19 vaccine provides robust protection against both ancestral and variant strains of SARS-CoV-2. Cell 185, 896-915.e19 (2022).
Al-Aly Z, Bowe B, & Xie Y. Long COVID after breakthrough SARS-CoV-2 infection. Nat. Med. 28, 1461-1467 (2022).
Allie, S. R. et al. The establishment of resident memory B cells in the lung requires local antigen encounter. Nat. Immunol. 20, 97-108 (2019).
An, Xingyue, et al., "Single-does intranasal vaccination elicits systemic and mucosal immunity agains SARS-CoV-2,", BioRxiv, (2020), XP093120206, DOI: 10.1101/2020.07.23.212357.
Andrews, M. G. et al. Tropism of SARS-CoV-2 for human cortical astrocytes. Proc. Natl. Acad. Sci. USA. 119(30), pp. 1-12, e2122236119 (2022).
Bai Y, et al.(2011) Intracellular neutralization of viral infection in polarized epithelial cells by neonatal Fc receptor (FcRn)-mediated IgG transport. Proc Natl Acad Sci U S A. 108:18406-11.
Baker K, et al.(2011) Neonatal Fc receptor for IgG (FcRn) regulates cross-presentation of IgG immune complexes by CD8-CD11b+ dendritic cells. Proc Natl Acad Sci U S A. 108:9927-32.
Bauer, L. et al. The neuroinvasiveness, neurotropism, and neurovirulence of SARS-CoV-2. Trends Neurosci. 45(5):358-368 (2022).
Barría MI, et al.(2013) Localized mucosal response to intranasal live attenuated influenza vaccine in adults. J Infect Dis. 207:115-24.
Brokstad KA (2002) Parenteral vaccination against influenza does not induce a local antigen-specific immune response in the nasal mucosa. J Infect Dis. 185:878-84.
Brown DM, et al. (2012) Multifunctional CD4 cells expressing gamma interferon and perforin mediate protection against lethal influenza virus infection. J Virol. 86:6792-803.
Chandrashekar, A. et al. Vaccine protection against the SARS-CoV-2 Omicron variant in macaques. Cell 185, 1549-1555.e11 (2022).
Chiu C, Openshaw PJ (2015) Antiviral B cell and T cell immunity in the lungs. Nat Immunol. 16:18-26.
Dan, J. M. et al. Immunological memory to SARS-CoV-2 assessed for up to 8 months after infection. Science 371, eabf4063 (2021).

(56) References Cited

OTHER PUBLICATIONS

Dekkers, G. et al. Affinity of human IgG subclasses to mouse Fc gamma receptors. MAbs 9, 767-773 (2017).

Dickinson BL, et al. (1999) Bidirectional FcRn-dependent IgG transport in a polarized human intestinal epithelial cell line. J Clin Invest. 104:903-11.

Du, L et al. The spike protein of SARS-CoV—a target for vaccine and therapeutic development. Nat. Rev. Microbiol. 7, 226-236 (2009).

Duncan AR, Winter G (1988) The binding site for C1q on IgG. Nature. 332:738-40.

Ekiert DC, et al. (2011) A highly conserved neutralizing epitope on group 2 influenza A viruses. Science. 333:843-50.

Erbelding EJ, et al. (2018) A Universal Influenza Vaccine: The Strategic Plan for the National Institute of Allergy and Infectious Diseases. J Infect Dis. 218:347-54.

Ermler ME, et al. (2017) Chimeric Hemagglutinin Constructs Induce Broad Protection against Influenza B Virus Challenge in the Mouse Model. J Virol. 91: pii: e00286-17.

Fischer, H. & Widdicombe, J. H. Mechanisms of acid and base secretion by the airway epithelium. J. Membr. Biol. 211, 139-150 (2006).

Frey A, Di Canzio J, Zurakowski D (1998) A statistically defined endpoint titer determination method for immunoassays. J. Immunol. Methods, 221:35-41.

Friesen RH, et al. (2014) A common solution to group 2 influenza virus neutralization. Proc Natl Acad Sci U S A. Jan. 7, 2014;111(1):445-50.

Fröberg, J et al. SARS-CoV-2 mucosal antibody development and persistence and their relation to viral load and COVID-19 symptoms. Nat. Commun. 12, 5621 (2021).

Golden, J. W. et al. Hamsters Expressing Human Angiotensin-Converting Enzyme 2 Develop Severe Disease following Exposure to SARS-CoV-2. mBio 13, e0290621(2022).

Grau-Expósito, J. et al. Peripheral and lung resident memory T cell responses against SARS-CoV-2. Nat. Commun. 12, 3010 (2021).

Hartwell, B. L. et al. Intranasal vaccination with lipid-conjugated immunogens promotes antigen transmucosal uptake to drive mucosal and systemic immunity. Sci. Transl. Med. 14(654), pp. 1-4, eabn1413 (2022).

Hassan, A. O. et al. A Single-Dose Intranasal ChAd Vaccine Protects Upper and Lower Respiratory Tracts against SARS-CoV-2. Cell 183, 169-184, e13 (2020).

He, W. et al. FcRn-mediated antibody transport across epithelial cells revealed by electron tomography. Nature 455, 542-546 (2008).

Hirst GK (1942) The Quantitative Determination of Influenza Virus and Abs by Means of Red Cell Agglutination. J. Exp. Med. 75:49-64.

Hodge LM, et al. (2001) Immunoglobulin A (IgA) responses and IgE-associated inflammation along the respiratory tract after mucosal but not systemic immunization. Infect Immun. 69:2328-38.

Hou, Y. J. et al. SARS-CoV-2 reverse genetics reveals a variable infection gradient in the respiratory tract. Cell 182, 429-446, e14 (2020).

Houser K, Subbarao K (2015) Influenza vaccines: challenges and solutions. Cell Host Microbe. 17:295-300.

Hunter, P. Viral diseases and the brain: Long COVID puts the spotlight on how viral infections affect the brain. EMBO Rep. 23, e54342 (2022).

Idusogie, E, E, et al. Mapping of the C1q binding site on rituxan, a chimeric antibody with a human IgG1 Fc. J. Immunol. 164, 4178-4184 (2000).

Iho S, Maeyama J, Suzuki F (2015) CpG oligodeoxynucleotides as mucosal adjuvants. Hum Vaccin Immunother. 11:755-60.

Iijima N, Iwasaki A (2015) Tissue instruction for migration and retention of TRM cells. Trends Immunol. 36:556-64.

Iwasaki A. (2016) Exploiting Mucosal Immunity for Antiviral Vaccines. Annu Rev Immunol. 34:575-608.

Iwasaki A, Foxman EF, Molony RD (2017) Early local immune defenses in the respiratory tract. Nat Rev Immunol. 17:7-20.

Jeyanathan, M. et al. Immunological considerations for COVID-19 vaccine strategies. Nat. Rev. Immunol. 20, 615-632 (2020).

Kim JK, Tsen MF, Ghetie V, Ward ES (1994) Localization of the site of the murine IgG1 molecule that is involved in binding to the murine intestinal Fc receptor. Eur J Immunol. 24:2429-34.

Ko SY, et al. (2014) Enhanced neonatal Fc receptor function improves protection against primate SHIV infection. Nature. 514:642-5.

Krammer F, et al. (2012) A carboxy-terminal trimerization domain stabilizes conformational epitopes on the stalk domain of soluble recombinant hemagglutinin substrates. PLoS One. 7:e43603.

Krammer F, Pica N, Hai R, Margine I, Palese P (2013) Chimeric hemagglutinin influenza virus vaccine constructs elicit broadly protective stalk-specific Abs. J Virol. 87:6542-50.

Krammer F, et al. (2014) Assessment of influenza virus hemagglutinin stalk-based immunity in ferrets. J Virol. 88:3432-42.

Krammer F, Palese P. (2015) Advances in the development of influenza virus vaccines. Nat Rev Drug Discov. 14:167-82.

Kubo T, et al. (2015) CpG-DNA enhances the tight junction integrity of the bronchial epithelial cell barrier. J Allergy Clin Immunol. 136:1413-6.

Laidlaw BJ, et al. (2014) CD4+ T cell help guides formation of CD103+ lung-resident memory CD8+ T cells during influenza viral infection. Immunity. 41:633-45.

Letarov AV, Londer YY, Boudko SP, Mesyanzhinov VV (1999) The carboxy-terminal domain initiates trimerization of bacteriophage T4 fibritin. Biochemistry (Mosc). 64:817-23.

Li, Jie, et al., "Immunogenicity and Protection Efficacy of Monomeric and Trimeric Recombinant SARS Coronavirus Spike Protein Subunit Vaccine Candidates," Viral Immunology, 26(2): 126-132 (2013).

Li, Weizhong, et al., "An FcRn-targeted mucosal vaccine against SARS-CoV-2 infection and transmission," bioRxiv (2022), XP093119729, DOI: 10.1101/2022.11.23.517678.

Li Z, et al. (2011) Transfer of IgG in the female genital tract by MHC class I-related neonatal Fc receptor (FcRn) confers protective immunity to vaginal infection. Proc Natl Acad Sci U S A. 108:4388-93.

Lipsitch, M., Krammer, F., Regev-Yochay, G., Lustig, Y., & Balicer, R.D. SARS-CoV-2 breakthrough infections in vaccinated individuals: measurement, causes and impact. Nat. Rev. Immunol. 22, 57-65 (2022).

Liu X, et al. (2011) The neonatal FcR-mediated presentation of immune-complexed antigen is associated with endosomal and phagosomal pH and antigen stability in macrophages and dendritic cells. J Immunol. 186:4674-86.

Lu et al. A neonatal Fc receptor-targeted mucosal vaccine strategy effectively induces HIV-1 antigen-specific immunity to genital infection. J Virol. Oct. 2011. Pages 10542-10553, vol. 85, No. 20.

Lund, F. E. & Randall, T. D. Scent of a vaccine. Science 373, 397-399 (2021).

McMaster SR, et al. (2018) Pulmonary antigen encounter regulates the establishment of tissue-resident CD8 memory T cells in the lung airways and parenchyma. Mucosal Immunol. 11:1071-8.

Major D, et al. (2015) Intranasal vaccination with a plant-derived H5 HA vaccine protects mice and ferrets against highly pathogenic avian influenza virus challenge. Hum Vaccin Immunother. 11:1235-43.

Mao, T. et al. Unadjuvanted intranasal spike vaccine elicits protective mucosal immunity against sarbecoviruses. Science 378(872), pp. 1-14, eabo2523 (2022).

Margine I, et al. (2013) Hemagglutinin stalk-based universal vaccine constructs protect against group 2 influenza A viruses. J Virol. 87:10435-46.

Meinhardt, J et al. Olfactory transmucosal SARS-CoV-2 invasion as a port of central nervous system entry in individuals with COVID-19. Nat. Neurosci. 24, 168-175 (2021).

Minne A, et al. (2007) The delivery site of a monovalent influenza vaccine within the respiratory tract impacts on the immune response. Immunology. 122:316-25.

Mueller SN, Gebhardt T, Carbone FR, Heath WR (2013) Memory T cell subsets, migration patterns, and tissue residence. Annu Rev Immunol. 31:137-61.

(56) References Cited

OTHER PUBLICATIONS

Muszkat M, et al. (2003) Local and systemic immune response in nursing-home elderly following intranasal or intramuscular immunization with inactivated influenza vaccine. Vaccine. 21:1180-6.
Ochsner, S. P et al. FcRn-Targeted Mucosal Vaccination against Influenza Virus Infection. *J Immunol*. 207(5), 1310-1321 (2021).
Oh S, et al. (2009) Neutralizing monoclonal Abs to different clades of Influenza A H5N1 viruses. J Virol Methods. 157:161-7.
Oh, J. E. et al. Intranasal priming induces local lung-resident B cell populations that secrete protective mucosal antiviral IgA. *Sci. Immunol*. 6, pp. 1-11, eabj5129 (2021).
Oladunni, F. S et al. Lethality of SARS-CoV-2 infection in K18 human angiotensin-converting enzyme 2 transgenic mice. *Nat. Commun*. 11, 6122 (2020).
Pallesen, J. et al. Immunogenicity and structures of a rationally designed prefusion MERS-CoV spike antigen. *Proc. Natl. Acad. Sci. U S A*. 114, E7348-E7357 (2017).
Pizzolla A, et al. (2017) Resident memory CD8+T cells in the upper respiratory tract prevent pulmonary influenza virus infection. Sci Immunol. 2. pii: eaam6970.
Planas, D. et al. Considerable escape of SARS-CoV-2 Omicron to antibody neutralization. *Nature* 602, 671-675 (2022).
Qiao SW, et al. (2008) Dependence of Ab mediated presentation of antigen on FcRn. Proc Natl Acad Sci U S A. 105:9337-42.
Renegar KB, Small PA Jr, Boykins LG, Wright PF (2004) Role of IgA versus IgG in the control of influenza viral infection in the murine respiratory tract. J Immunol. 173:1978-86.
Roukens, A. H. E et al. Prolonged activation of nasal immune cell populations and development of tissue-resident SARS-CoV-2-specific CD8+ T cell responses following COVID-19. *Nat. Immunol*. 23, 23-32 (2022).
Russell, M. W. & Mestecky, J. Mucosal immunity: The missing link in comprehending SARS-CoV-2 infection and transmission. *Front Immunol*. 13: 957107 (2022).
Sakurai, A. et al. Natural History of Asymptomatic SARS-CoV-2 Infection. *N. Engl. J. Med*. 383, 885-886 (2020).
Sallusto F, Lanzavecchia A, Araki K, Ahmed R (2010) From vaccines to memory and back. Immunity. 33:451-63.
Sia, S. F et al. Pathogenesis and transmission of SARS-CoV-2 in golden hamsters. *Nature* 583, 834-838 (2020).
Slifka MK, Antia R, Whitmire JK, Ahmed R (1998) Humoral immunity due to long-lived plasma cells. Immunity. 8:363-72.
Slütter B, et al. (2017) Dynamics of influenza-induced lung-resident memory T cells underlie waning heterosubtypic immunity. Sci Immunol. 2. pii: eaag2031.
Spiekermann GM, et al. (2002) Receptor-mediated immunoglobulin G transport across mucosal barriers in adult life: functional expression of FcRn in the mammalian lung. J Exp Med. 196:303-10.
Sterlin, D. et al. IgA dominates the early neutralizing antibody response to SARS-CoV-2. *Sci. Transl. Med*. 13, pp. 1-10, eabd2223 (2021).
Sui, Y. et al. Protection against SARS-CoV-2 infection by a mucosal vaccine in rhesus macaques. JCI Insight. Apr. 28, 2021;6(10): e148494.
Szabo, P. A., Miron, M., & Farber, D. L. Location, location, location: Tissue resident memory T cells in mice and humans. Sci. Immunol. 4(34), eaas9673 (2019).

Tan GS, et al. (2012) A pan-H1 anti-hemagglutinin monoclonal Ab with potent broad-spectrum efficacy in vivo. J Virol. 86:6179-88.
Tang, J. et al. Respiratory mucosal immunity against SARS-CoV-2 after mRNA vaccination. *Sci. Immunol*. 7(76), eadd4853 (2022).
Turner DL, Farber DL (2014) Mucosal resident memory CD4 T cells in protection and immunopathology. Front Immunol. 14;5:331.
Van Doremalen, N et al. ChAdOx1 nCOV-19 vaccine prevents SARS-COV-2 pneumonia in rhesus macaques. *Nature* 586, 578-592 (2020). Erratum in: *Nature* 590, E24 (2021).
van Riet E, Ainai A, Suzuki T, Hasegawa H (2012) Mucosal IgA responses in influenza virus infections; thoughts for vaccine design. Vaccine. 30:5893-900.
Vaughn DE, Bjorkman PJ. (1998) Structural basis of pH-dependent Ab binding by the neonatal Fc receptor. Structure. 6:63-73.
V'kovski, P., Kratzel, A., Steiner, S., Stalder, H., & Thiel, V. Coronavirus biology and replication: implications for SARS-CoV-2. *Nat. Rev. Microbiol*. 19, 155-170 (2021).
Walls et al. "Structure, function and antigenicity of the SARS-CoV-2 spike glycoprotein" bioRxiv, Feb. 20, 2020; Cell 180, 281-292, Apr. 16, 2020.
Ward, E.S., Zhou, J., Ghetie, V., & Ober, R. J. Evidence to support the cellular mechanism involved in serum IgG homeostasis in humans. *Int. Immunol*. 15, 187-195 (2003).
Weldon WC, et al. (2010) Enhanced immunogenicity of stabilized trimeric soluble influenza hemagglutinin. PLoS One. 5. pii: e12466.
Wrapp et al., "Cryo-EM structure of the 2019-nCOV spike in the prefusion conformation," Science 367:1260-1263 (2020), 4 Pages.
Wu T, et al. (2014) Lung-resident memory CD8 T cells (TRM) are indispensable for optimal cross-protection against pulmonary virus infection. J Leukoc Biol. 95:215-24.
Yen, H. L. et al. Transmission of SARS-CoV-2 delta variant (AY.127) from pet hamsters to humans, leading to onward human-to-human transmission: a case study. *Lancet* 399, 1070-1078 (2022).
Yoshida, M. et al. Human neonatal Fc receptor mediates transport of IgG into luminal secretions for delivery of antigens to mucosal dendritic cells. *Immunity* 20, 769-783 (2004).
Yoshida M, et al. (2006) Neonatal Fc receptor for IgG regulates mucosal immune responses to luminal bacteria. J Clin Invest. 116:2142-2151.
Zeng, et al. SARS-CoV-2 spreads through cell-to-cell transmission. *Proc. Natl. Acad. Sci. U S A*. 119(1), e2111400119 (2022).
Zens KD, Chen JK, Farber DL (2016) Vaccine-generated lung tissue-resident memory T cells provide heterosubtypic protection to influenza infection. JCI Insight. 1. pii: e85832.
Zhirnov OP, Ikizler MR, Wright PF (2002) Cleavage of influenza a virus hemagglutinin in human respiratory epithelium is cell associated and sensitive to exogenous antiproteases. J Virol. 76:8682-9.
Zhou, D. et al. Robust SARS-CoV-2 infection in nasal turbinates after treatment with systemic neutralizing antibodies. *Cell Host Microbe*. 29(4), 551-563.e5 (2021).
Written Opinion and Search Report issued Jul. 1, 2021 by the International Search Report for Application No. PCT/US2021/020099 filed on Feb. 26, 2021 (Applicant: University of Maryland) (11 pages).
European Extended Search Report mailed Jan. 29, 2024 for EP 21760268.9, PCT/US2021/020099, filed Oct. 15, 2018.
International Search Report and Written Opinion mailed Feb. 22, 2019 for PCT/US2018/55896, filed Oct. 15, 2018, (14 Pages).

\* cited by examiner

FIG. 1

SEQUENCE LISTING

```
<160> NUMBER OF SEQ ID NOS: 14

<210> SEQ ID NO 1
<211> LENGTH: 804
<212> TYPE: PRT
<213> ORGANISM: Artificial Sequence
<220> FEATURE:
<223> OTHER INFORMATION: synthetic construct

<400> SEQUENCE: 1

Met Pro Met Gly Ser Leu Gln Pro Leu Ala Thr Leu Tyr Leu Leu Gly
1               5                   10                  15

Met Leu Val Ala Ser Cys Leu Gly Gln Asn Ile Thr Glu Glu Phe Tyr
            20                  25                  30

Gln Ser Thr Cys Ser Ala Val Ser Lys Gly Tyr Leu Ser Ala Leu Arg
        35                  40                  45

Thr Gly Trp Tyr Thr Ser Val Ile Thr Ile Glu Leu Ser Asn Ile Lys
    50                  55                  60

Glu Asn Lys Cys Asn Gly Thr Asp Ala Lys Val Lys Leu Ile Lys Gln
65                  70                  75                  80

Glu Leu Asp Lys Tyr Lys Asn Ala Val Thr Glu Leu Gln Leu Leu Met
                85                  90                  95

Gln Ser Thr Pro Ala Thr Asn Asn Arg Ala Arg Arg Glu Leu Pro Arg
            100                 105                 110

Phe Met Asn Tyr Thr Leu Asn Asn Ala Lys Lys Thr Asn Val Thr Leu
        115                 120                 125

Ser Lys Lys Arg Lys Arg Arg Phe Leu Gly Phe Leu Leu Gly Val Gly
    130                 135                 140

Ser Ala Ile Ala Ser Gly Val Ala Val Cys Lys Val Leu His Leu Glu
145                 150                 155                 160

Gly Glu Val Asn Lys Ile Lys Ser Ala Leu Leu Ser Thr Asn Lys Ala
                165                 170                 175

Val Val Ser Leu Ser Asn Gly Val Ser Val Leu Thr Phe Lys Val Leu
            180                 185                 190

Asp Leu Lys Asn Tyr Ile Asp Lys Gln Leu Leu Pro Ile Leu Asn Lys
        195                 200                 205

Gln Ser Cys Ser Ile Ser Asn Ile Glu Thr Val Ile Glu Phe Gln Gln
    210                 215                 220

Lys Asn Asn Arg Leu Leu Glu Ile Thr Arg Glu Phe Ser Val Asn Ala
225                 230                 235                 240

Gly Val Thr Thr Pro Val Ser Thr Tyr Met Leu Thr Asn Ser Glu Leu
                245                 250                 255

Leu Ser Leu Ile Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
        275                 280                 285

Cys Ile Ile Lys Glu Glu Val Leu Ala Tyr Val Val Gln Leu Pro Leu
    290                 295                 300

Tyr Gly Val Ile Asp Thr Pro Cys Trp Lys Leu His Thr Ser Pro Leu
305                 310                 315                 320
```

```
Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
        355                 360                 365

Met Asn Ser Leu Thr Leu Pro Ser Glu Val Asn Leu Cys Asn Val Asp
    370                 375                 380

Ile Phe Asn Pro Lys Tyr Asp Cys Lys Ile Met Thr Ser Lys Thr Asp
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
        435                 440                 445

Val Ser Val Gly Asn Thr Leu Tyr Tyr Val Asn Lys Gln Glu Gly Lys
    450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
                485                 490                 495

Lys Ile Asn Gln Ser Leu Ala Phe Ile Arg Lys Ser Asp Glu Leu Leu
            500                 505                 510

Gly Ser Gly Ser Gly Ser Arg Ser Leu Val Pro Arg Gly Ser Pro Gly
        515                 520                 525

Ser Gly Tyr Ile Pro Glu Ala Pro Arg Asp Gly Gln Ala Tyr Val Arg
    530                 535                 540

Lys Asp Gly Glu Trp Val Leu Leu Ser Thr Phe Leu Gly Gly Ser Gly
545                 550                 555                 560

Gly Gly Gly Ser Gly Gly Gly Ser Gly Ser Glu Pro Arg Gly Pro
                565                 570                 575

Thr Ile Lys Pro Ser Pro Ser Lys Ser Pro Ala Pro Asn Leu Leu
            580                 585                 590

Gly Gly Pro Ser Val Phe Ile Phe Pro Pro Lys Ile Lys Asp Val Leu
        595                 600                 605

Met Ile Ser Leu Ser Pro Ile Val Thr Cys Val Val Val Asp Val Ser
    610                 615                 620

Glu Asp Asp Pro Asp Val Gln Ile Ser Trp Phe Val Asn Asn Val Glu
625                 630                 635                 640

Val His Thr Ala Gln Thr Gln Thr His Arg Glu Asp Tyr Asn Ser Thr
                645                 650                 655

Leu Arg Val Val Ser Ala Leu Pro Ile Gln His Gln Asp Trp Met Ser
            660                 665                 670

Gly Lys Ala Phe Ala Cys Ala Val Asn Asn Lys Asp Leu Pro Ala Pro
        675                 680                 685

Ile Glu Arg Thr Ile Ser Lys Pro Lys Gly Ser Val Arg Ala Pro Gln
    690                 695                 700

Val Tyr Val Leu Pro Pro Pro Glu Glu Glu Met Thr Lys Lys Gln Val
705                 710                 715                 720

Thr Leu Thr Cys Met Val Thr Asp Phe Met Pro Glu Asp Ile Tyr Val
                725                 730                 735
```

```
Glu Trp Thr Asn Asn Gly Lys Thr Glu Leu Asn Tyr Lys Asn Thr Glu
            740                 745                 750
Pro Val Leu Asp Ser Asp Gly Ser Tyr Phe Met Tyr Ser Lys Leu Arg
            755                 760                 765
Val Glu Lys Lys Asn Trp Val Glu Arg Asn Ser Tyr Ser Cys Ser Val
770                 775                 780
Val His Glu Gly Leu His Asn His His Thr Thr Lys Ser Phe Ser Arg
785                 790                 795                 800
Thr Pro Gly Lys

<210> SEQ ID NO 2
<211> LENGTH: 233
<212> TYPE: PRT
<213> ORGANISM: Artificial Sequence
<220> FEATURE:
<223> OTHER INFORMATION: synthetic construct

<400> SEQUENCE: 2

Glu Pro Arg Gly Pro Thr Ile Lys Pro Ser Pro Ser Lys Ser Pro
1               5                   10                  15
Ala Pro Asn Leu Leu Gly Gly Pro Ser Val Phe Ile Phe Pro Pro Lys
            20                  25                  30
Ile Lys Asp Val Leu Met Ile Ser Leu Ser Pro Ile Val Thr Cys Val
            35                  40                  45
Val Val Asp Val Ser Glu Asp Asp Pro Asp Val Gln Ile Ser Trp Phe
    50                  55                  60
Val Asn Asn Val Glu Val His Thr Ala Gln Thr Gln Thr His Arg Glu
65                  70                  75                  80
Asp Tyr Asn Ser Thr Leu Arg Val Val Ser Ala Leu Pro Ile Gln His
                85                  90                  95
Gln Asp Trp Met Ser Gly Lys Ala Phe Ala Cys Ala Val Asn Asn Lys
            100                 105                 110
Asp Leu Pro Ala Pro Ile Glu Arg Thr Ile Ser Lys Pro Lys Gly Ser
            115                 120                 125
Val Arg Ala Pro Gln Val Tyr Val Leu Pro Pro Pro Glu Glu Glu Met
    130                 135                 140
Thr Lys Lys Gln Val Thr Leu Thr Cys Met Val Thr Asp Phe Met Pro
145                 150                 155                 160
Glu Asp Ile Tyr Val Glu Trp Thr Asn Asn Gly Lys Thr Glu Leu Asn
                165                 170                 175
Tyr Lys Asn Thr Glu Pro Val Leu Asp Ser Asp Gly Ser Tyr Phe Met
            180                 185                 190
Tyr Ser Lys Leu Arg Val Glu Lys Lys Asn Trp Val Glu Arg Asn Ser
            195                 200                 205
Tyr Ser Cys Ser Val Val His Glu Gly Leu His Asn His His Thr Thr
    210                 215                 220
Lys Ser Phe Ser Arg Thr Pro Gly Lys
225                 230

<210> SEQ ID NO 3
<211> LENGTH: 699
<212> TYPE: DNA
<213> ORGANISM: Artificial Sequence
<220> FEATURE:
<223> OTHER INFORMATION: synthetic construct
```

<400> SEQUENCE: 3

```
gagcccagag ggcccacaat caagccctct cctccatcca aatccccagc acctaacctc        60
ttgggtggac catccgtctt catcttccct ccaaagatca aggatgtact catgatctcc       120
ctgagcccca tagtcacatg tgtggtggtg gatgtgagcg aggatgaccc agatgtccag       180
atcagctggt ttgtgaacaa cgtggaagta cacacagctc agacacaaac ccatagagag       240
gattacaaca gtactctccg ggtggtcagt gccctcccca tccagcacca ggactggatg       300
agtggcaagg cgttcgcatg cgcggtcaac aacaaagacc tcccagcgcc catcgagaga       360
accatctcaa aacccaaagg gtcagtaaga gctccacagg tatatgtctt gcctccacca       420
gaagaagaga tgactaagaa acaggtcact ctgacctgca tggtcacaga cttcatgcct       480
gaagacattt acgtggagtg gaccaacaac gggaaaacag agctaaacta caagaacact       540
gaaccagtcc tggactctga tggttcttac ttcatgtaca gcaagctgag agtggaaaag       600
aagaactggg tggaaagaaa tagctactcc tgttcagtgg tccacgaggg tctgcacaat       660
caccacacga ctaagagctt ctcccggact ccgggtaaa                              699
```

<210> SEQ ID NO 4
<211> LENGTH: 233
<212> TYPE: PRT
<213> ORGANISM: Artificial Sequence
<220> FEATURE:
<223> OTHER INFORMATION: synthetic construct

<400> SEQUENCE: 4

```
Glu Pro Arg Gly Pro Thr Ile Lys Pro Ser Pro Ser Lys Ser Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln Ala
                85                  90                  95

Asp Asp Trp Met Ser Gly Lys Ala Phe Ala Cys Ala Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu Ala Gln His His Thr Thr
    210                 215                 220
```

```
Lys Ser Phe Ser Arg Thr Pro Gly Lys
225                 230
```

<210> SEQ ID NO 5
<211> LENGTH: 699
<212> TYPE: DNA
<213> ORGANISM: Artificial Sequence
<220> FEATURE:
<223> OTHER INFORMATION: synthetic construct

<400> SEQUENCE: 5
gagcccagag ggcccacaat caagccctct cctccatcca aatccccagc acctaacctc 60
ttgggtggac catccgtctt catcttccct ccaaagatca aggatgtact catgatctcc 120
ctgagcccca tagtcacatg tgtggtggtg gatgtgagcg aggatgaccc agatgtccag 180
atcagctggt ttgtgaacaa cgtggaagta cacacagctc agacacaaac ccatagagag 240
gattacaaca gtactctccg ggtggtcagt gccctcccca tccaggccga cgactggatg 300
agtggcaagg cgttcgcatg cgcggtcaac aacaaagacc tcccagcgcc catcgagaga 360
accatctcaa aacccaaagg gtcagtaaga gctccacagg tatatgtctt gcctccacca 420
gaagaagaga tgactaagaa acaggtcact ctgacctgca tggtcacaga cttcatgcct 480
gaagacattt acgtggagtg gaccaacaac gggaaaacag agctaaacta caagaacact 540
gaaccagtcc tggactctga tggttcttac ttcatgtaca gcaagctgag agtggaaaag 600
aagaactggg tggaaagaaa tagctactcc tgttcagtgg tccacgaggg tctggcccaa 660
caccacacga ctaagagctt ctcccggact ccgggtaaa 699

<210> SEQ ID NO 6
<211> LENGTH: 574
<212> TYPE: PRT
<213> ORGANISM: respiratory syncytial virus

<400> SEQUENCE: 6

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Pro Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Ile Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 7
<211> LENGTH: 488

```
<212> TYPE: PRT
<213> ORGANISM: Artificial Sequence
<220> FEATURE:
<223> OTHER INFORMATION: synthetic construct

<400> SEQUENCE: 7

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
                20                  25                  30

Thr Ile Glu Leu Ser Asn Ile Lys Glu Asn Lys Cys Asn Gly Thr Asp
                35                  40                  45

Ala Lys Val Lys Leu Ile Lys Gln Glu Leu Asp Lys Tyr Lys Asn Ala
            50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
            115                 120                 125

Val Cys Lys Val Leu His Leu Glu Gly Glu Val Asn Lys Ile Lys Ser
130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190

Glu Thr Val Ile Glu Phe Gln Gln Lys Asn Asn Arg Leu Leu Glu Ile
            195                 200                 205

Thr Arg Glu Phe Ser Val Asn Ala Gly Val Thr Thr Pro Val Ser Thr
210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Cys Ile Ile Lys Glu Glu Val Leu
            260                 265                 270

Ala Tyr Val Val Gln Leu Pro Leu Tyr Gly Val Ile Asp Thr Pro Cys
            275                 280                 285

Trp Lys Leu His Thr Ser Pro Leu Cys Thr Thr Asn Thr Lys Glu Gly
290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Val Asp Ile Phe Asn Pro Lys Tyr Asp Cys
            355                 360                 365

Lys Ile Met Thr Ser Lys Thr Asp Val Ser Ser Ser Val Ile Thr Ser
            370                 375                 380
```

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
            405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
            435                 440                 445

Ile Ile Asn Phe Tyr Asp Pro Leu Val Phe Pro Ser Asp Glu Phe Asp
            450                 455                 460

Ala Ser Ile Ser Gln Val Asn Glu Lys Ile Asn Gln Ser Leu Ala Phe
465                 470                 475                 480

Ile Arg Lys Ser Asp Glu Leu Leu
                485

<210> SEQ ID NO 8
<211> LENGTH: 1464
<212> TYPE: DNA
<213> ORGANISM: Artificial Sequence
<220> FEATURE:
<223> OTHER INFORMATION: synthetic construct

<400> SEQUENCE: 8
cagaacatca ccgaggaatt ctaccagagc acctgcagcg ccgtgagcaa gggctacctg      60
agcgccctgc ggaccggctg gtacaccagc gtgatcacca tcgagctgtc caacatcaaa     120
gaaaacaagt gcaacggcac cgacgccaaa gtgaagctga tcaagcagga actggacaag     180
tacaagaacg ccgtgaccga gctgcagctg ctgatgcaga gcacccccgc caccaacaac     240
agagccagaa gagagctgcc ccggttcatg aactacaccc tgaacaacgc caagaaaacc     300
aacgtgaccc tgagcaagaa gagaaagaga agattcctgg gcttcctgct gggcgtgggc     360
agcgccattg ccagcggcgt ggccgtgtgt aaagtgctgc acctggaagg cgaagtgaac     420
aagatcaagt ccgccctgct gtccaccaac aaggccgtgg tgtccctgag caacggcgtg     480
agcgtgctga ccttcaaggt gctggatctg aagaactaca tcgacaagca gctgctgccc     540
atcctgaaca gcagagctg cagcatcagc aacatcgaga cagtgatcga gttccagcag     600
aagaacaacc ggctgctgga aatcacccgg gagttcagcg tgaacgccgg agtgaccacc     660
cccgtgtcca cctacatgct gaccaacagc gagctgctgt ccctgatcaa tgacatgccc     720
atcaccaacg accagaaaaa gctgatgagc aacaacgtgc agatcgtgcg gcagcagagc     780
tacagcatca tgtgcatcat caaagaagag gtgctggcct acgtggtgca gctgcccctg     840
tacggcgtga tcgacacccc ctgctggaag ctgcacacca gccccctgtg cacaaccaac     900
accaaagagg gcagcaacat ctgcctgacc cggaccgacc ggggctggta ctgcgacaac     960
gccggcagcg tgtctttctt ccacaggcc gagacatgca aggtgcagag caaccgggtg    1020
ttctgcgaca ccatgaacag cctgaccctg ccctccgaag tgaacctgtg caacgtggac    1080
atcttcaacc ccaagtacga ctgcaagatc atgacctcca agaccgacgt gtccagctcc    1140
gtgatcacct ccctgggcgc catcgtgtcc tgctacggca gaccaagtg caccgccagc    1200 aacaagaaca gaggcatcat caagaccttc agcaacggct gcgactacgt gtccaataag    1260
ggcgtggaca ccgtgtccgt gggcaacaca ctgtactacg tgaataagca ggaaggcaag    1320
agcctgtacg tgaagggcga gcccatcatc aacttctacg acccctggt gttccccagc    1380

```
gacgagttcg acgccagcat cagccaggtg aacgagaaga tcaaccagag cctggccttc    1440
atcagaaaga gcgacgaact gctg                                           1464
```

<210> SEQ ID NO 9
<211> LENGTH: 29
<212> TYPE: PRT
<213> ORGANISM: Artificial Sequence
<220> FEATURE:
<223> OTHER INFORMATION: synthetic construct

<400> SEQUENCE: 9

```
Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25
```

<210> SEQ ID NO 10
<211> LENGTH: 87
<212> TYPE: DNA
<213> ORGANISM: Artificial Sequence
<220> FEATURE:
<223> OTHER INFORMATION: synthetic construct

<400> SEQUENCE: 10

```
ggcagcggct acatccccga ggcccccaga gacggccagg cctacgtgag aaaggacggc    60
gagtgggtgc tgctgagcac cttcctg                                        87
```

<210> SEQ ID NO 11
<211> LENGTH: 32
<212> TYPE: PRT
<213> ORGANISM: Artificial Sequence
<220> FEATURE:
<223> OTHER INFORMATION: synthetic construct

<400> SEQUENCE: 11

```
Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30
```

<210> SEQ ID NO 12
<211> LENGTH: 6
<212> TYPE: PRT
<213> ORGANISM: Artificial Sequence
<220> FEATURE:
<223> OTHER INFORMATION: synthetic construct

<400> SEQUENCE: 12

```
Gly Ser Gly Ser Gly Ser
1               5
```

<210> SEQ ID NO 13
<211> LENGTH: 14
<212> TYPE: PRT
<213> ORGANISM: Artificial Sequence
<220> FEATURE:
<223> OTHER INFORMATION: synthetic construct

<400> SEQUENCE: 13

```
Gly Ser Gly Gly Gly Gly Ser Gly Gly Gly Gly Ser Gly Ser
1               5                   10
```

<210> SEQ ID NO 14

<211> LENGTH: 2415
<212> TYPE: DNA
<213> ORGANISM: Artificial Sequence
<220> FEATURE:
<223> OTHER INFORMATION: synthetic construct

<400> SEQUENCE: 14

| | | | | | |
|---|---|---|---|---|---|
| atgcccatgg | ggtctctgca | accgctggcc | accttgtacc | tgctggggat | gctggtcgct | 60 |
| tcctgcctcg | acagaacat | caccgaggaa | ttctaccaga | gcacctgcag | cgccgtgagc | 120 |
| aagggctacc | tgagcgccct | gcggaccggc | tggtacacca | gcgtgatcac | catcgagctg | 180 |
| tccaacatca | agaaaaacaa | gtgcaacggc | accgacgcca | agtgaagct | gatcaagcag | 240 |
| gaactggaca | agtacaagaa | cgccgtgacc | gagctgcagc | tgctgatgca | gagcaccccc | 300 |
| gccaccaaca | cagagccag | aagagagctg | ccccggttca | tgaactacac | cctgaacaac | 360 |
| gccaagaaaa | ccaacgtgac | cctgagcaag | aagagaaaga | aagattcct | gggcttcctg | 420 |
| ctgggcgtgg | gcagcgccat | tgccagcggc | gtggccgtgt | gtaaagtgct | gcacctggaa | 480 |
| ggcgaagtga | acaagatcaa | gtccgccctg | ctgtccacca | caaggccgt | ggtgtccctg | 540 |
| agcaacggcg | tgagcgtgct | gaccttcaag | gtgctggatc | tgaagaacta | catcgacaag | 600 |
| cagctgctgc | ccatcctgaa | caagcagagc | tgcagcatca | gcaacatcga | cagtgatc | 660 |
| gagttccagc | agaagaacaa | ccggctgctg | gaaatcaccc | gggagttcag | cgtgaacgcc | 720 |
| ggagtgacca | cccccgtgtc | cacctacatg | ctgaccaaca | gcgagctgct | gtccctgatc | 780 |
| aatgacatgc | ccatcaccaa | cgaccagaaa | agctgatga | gcaacaacgt | gcagatcgtg | 840 |
| cggcagcaga | gctacagcat | catgtgcatc | atcaaagaag | aggtgctggc | ctacgtggtg | 900 |
| cagctgcccc | tgtacggcgt | gatcgacacc | ccctgctgga | agctgcacac | cagcccctg | 960 |
| tgcacaacca | caccaaaga | gggcagcaac | atctgcctga | cccggaccga | ccggggctgg | 1020 |
| tactgcgaca | acgccggcag | cgtgtctttc | tttccacagg | ccgagacatg | caaggtgcag | 1080 |
| agcaaccggg | tgttctgcga | caccatgaac | agcctgaccc | tgcccctccga | agtgaacctg | 1140 |
| tgcaacgtgg | acatcttcaa | ccccaagtac | gactgcaaga | tcatgacctc | aagaccgac | 1200 |
| gtgtccagct | ccgtgatcac | ctccctgggc | gccatcgtgt | cctgctacgg | caagaccaag | 1260 |
| tgcaccgcca | gcaacaagaa | cagaggcatc | atcaagacct | tcagcaacgg | ctgcgactac | 1320 |
| gtgtccaata | agggcgtgga | caccgtgtcc | gtgggcaaca | cactgtacta | cgtgaataag | 1380 |
| caggaaggca | agagcctgta | cgtgaagggc | gagcccatca | tcaacttcta | cgaccccctg | 1440 |
| gtgttcccca | gcgacgagtt | cgacgccagc | atcagccagg | tgaacgagaa | gatcaaccag | 1500 |
| agcctggcct | tcatcagaaa | gagcgacgaa | ctgctgggat | caggctcagg | atcaagaagc | 1560 |
| ctggtgccca | gaggcagccc | cggcagcggc | tacatccccg | aggcccccag | agacggccag | 1620 |
| gcctacgtga | aaaggacgg | cgagtgggtg | ctgctgagca | ccttcctggg | cggatcaggc | 1680 |
| gggggtgggt | ccgagggagg | tggctcggga | tctgagccca | gagggcccac | aatcaagccc | 1740 |
| tctcctccat | ccaaatcccc | agcacctaac | ctcttgggtg | gaccatccgt | cttcatcttc | 1800 |
| cctccaaaga | tcaaggatgt | actcatgatc | tccctgagcc | ccatagtcac | atgtgtggtg | 1860 |
| gtggatgtga | gcgaggatga | cccagatgtc | cagatcagct | ggtttgtgaa | caacgtggaa | 1920 |
| gtacacacag | ctcagacaca | aacccataga | gaggattaca | acagtactct | ccgggtggtc | 1980 |
| agtgccctcc | ccatccagca | ccaggactgg | atgagtggca | aggcgttcgc | atgcgcggtc | 2040 |
| aacaacaaag | acctcccagc | gcccatcgag | agaaccatct | caaaacccaa | agggtcagta | 2100 |
| agagctccac | aggtatatgt | cttgcctcca | ccagaagaag | agatgactaa | gaaacaggtc | 2160 |

```
actctgacct gcatggtcac agacttcatg cctgaagaca tttacgtgga gtggaccaac    2220
aacgggaaaa cagagctaaa ctacaagaac actgaaccag tcctggactc tgatggttct    2280
tacttcatgt acagcaagct gagagtggaa aagaagaact gggtggaaag aaatagctac    2340
tcctgttcag tggtccacga gggtctgcac aatcaccaca cgactaagag cttctcccgg    2400
actccgggta aataa                                                    2415
```

FcRn-TARGETED MUCOSAL VACCINATION AGAINST RSV

CROSS-REFERENCE TO RELATED APPLICATIONS

This application is a continuation of application Ser. No. 16/117,915 filed Aug. 30, 2018 which claims the benefit of U.S. Provisional Application No. 62/552,041 filed Aug. 30, 2017. The content of these earlier filed application are hereby incorporated by reference in their entirety.

STATEMENT REGARDING FEDERALLY SPONSORED RESEARCH

The Sequence Listing submitted Aug. 17, 2022 as a text file named "36429_0008U2_Sequence_Listing.txt," created on Jun. 3, 2022, and having a size of 29,557 bytes is hereby incorporated by reference pursuant to 37 C.F.R. § 1.52(e)(5).

REFERENCE TO SEQUENCE LISTING

The Sequence Listing submitted Aug. 30, 2018 as a text file named "36429_0008U1_Sequence_Listing.txt," created on Aug. 30, 2018, and having a size of 29,517 bytes is hereby incorporated by reference pursuant to 37 C.F.R. § 1.52(e)(5).

BACKGROUND

Respiratory syncytial virus (RSV) infects the lower respiratory tract by spreading through coughing and sneezing. When infected, healthy people usually have mild, col-like symptoms and recover in a week or two. However, the infection can be very serious, especially for infants and older adults. Virtually all infants or older adults are potentially infected with RSV and 1-2%, or even more, of all infected children or older adults require intensive care treatment in a hospital. Also, RSV infection of children has been implicated in facilitating asthma development. Despite the significant health and economic burden, a safe and effective RSV vaccine has yet to be approved. Hence, an ideal RSV vaccine is being developed towards blocking virus replication and avoiding vaccine-associated side effects in people at high risk for severe RSV infection. The current studies have shown that the neonatal Fc receptor (FcRn) can efficiently transport vaccine antigens across the mucosal barrier to produce the protective immunity against mucosal infections.

BRIEF SUMMARY

Disclosed are peptides comprising a monomeric Fc fragment of an immunoglobulin recognized by a neonatal receptor (FcRn); a modified pre-fusion respiratory syncytia virus (RSV) F protein; and a trimerization domain.

Disclosed are compositions comprising peptides comprising a monomeric Fc fragment of an immunoglobulin recognized by a neonatal receptor (FcRn); a modified pre-fusion respiratory syncytia virus (RSV) F protein; and a trimerization domain.

Disclosed are nucleic acid sequences capable of encoding peptides comprising a monomeric Fc fragment of an immunoglobulin recognized by a neonatal receptor (FcRn); a modified pre-fusion respiratory syncytia virus (RSV) F protein; and a trimerization domain.

Disclosed are methods for eliciting a protective immune response against RSV comprising administering to a subject an effective amount of a composition comprising a monomeric Fc fragment of an immunoglobulin recognized by FcRn; a modified pre-fusion RSV F protein; and a trimerization domain, wherein the administering is to a mucosal epithelium.

Disclosed are methods of treating a subject exposed to RSV or at risk of being exposed to RSV comprising administering to the subject an effective amount of a composition comprising a monomeric Fc fragment of an immunoglobulin recognized by FcRn; a modified pre-fusion RSV F protein; and a trimerization domain, wherein the administering is to a mucosal epithelium.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

Figure 1:
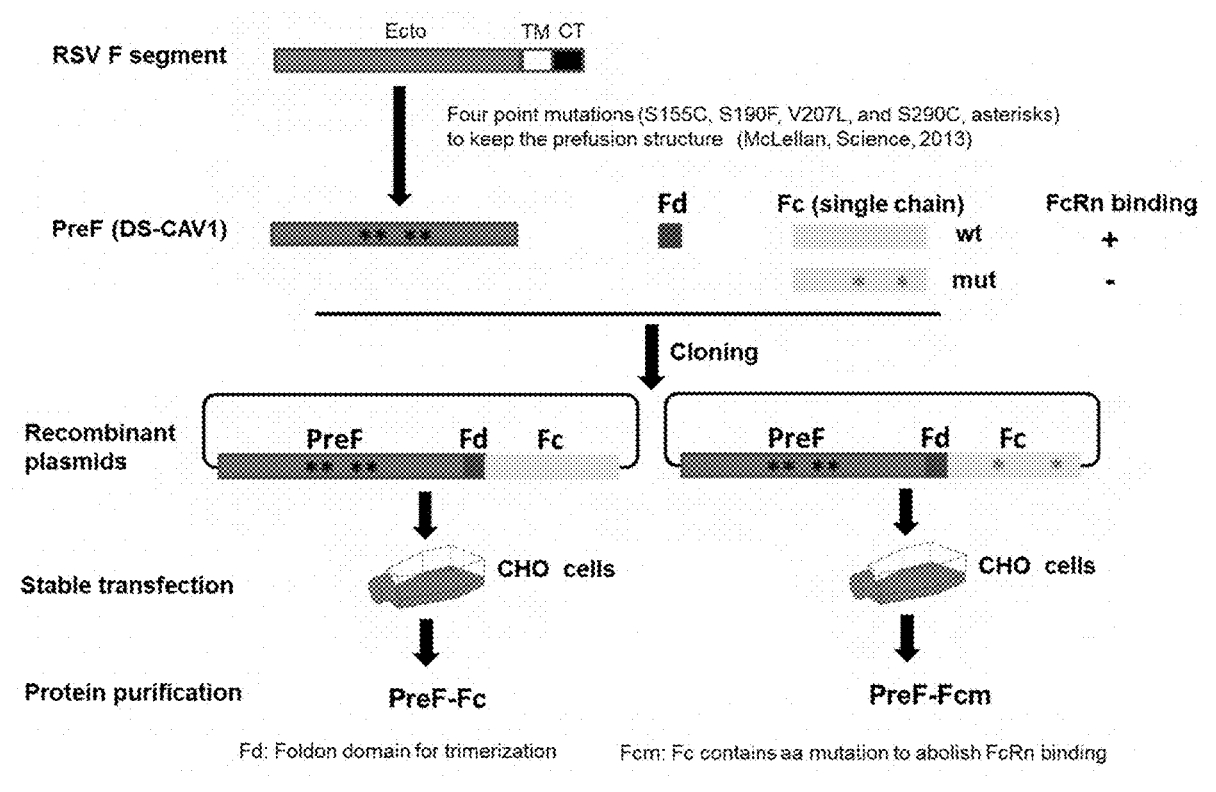

FIG. 1 is a schematic diagram of the generation of a peptide comprising a monomeric Fc fragment of an immunoglobulin recognized by a FcRn; a modified pre-fusion RSV F protein; and a trimerization domain.

DETAILED DESCRIPTION

Figure 2:
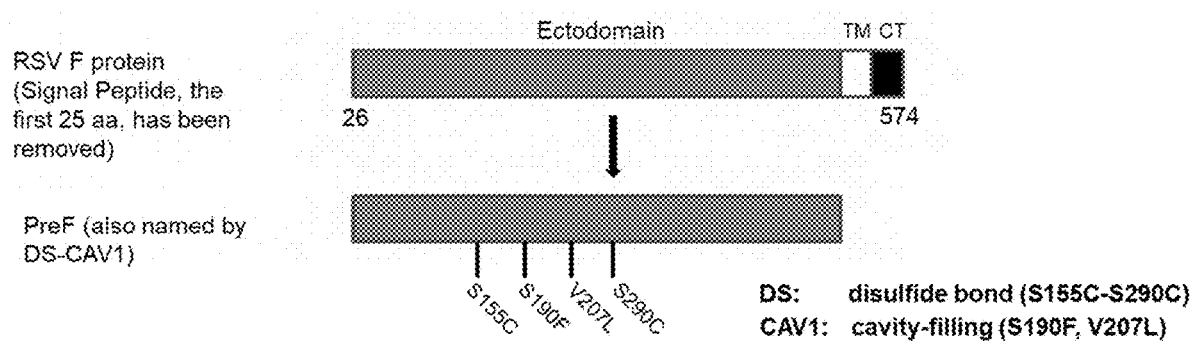
FIG. 2 is a schematic diagram of the RSV F protein and modified pre-fusion RSV F protein.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the amino acids are discussed, each and every combination and permutation of the peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E. and F; and the example combination A-D. Likewise, any subset or combination of these is also specifically contemplated and disclosed. Thus, for example, the sub-group of A-E, B-F. and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

The terminology used herein is for the purpose of describing particular embodiments only and is not intended to be limiting.

The word "or" as used herein means any one member of a particular list and also includes any combination of members of that list.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example. "treating" RSV may refer to inhibiting survival, growth, and/or spread of the virus. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

"Optional" or"optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; and Y, tyrosine.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "subject" refers to the target of administration. e.g. an animal. Thus the subject of the disclosed methods can be a vertebrate, such as a mammal. For example, the subject can be a human. The term does not denote a particular age or sex. Subject can be used interchangeably with "individual" or "patient".

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Peptides

Disclosed are peptides comprising a monomeric Fc fragment of an immunoglobulin recognized by a neonatal receptor (FcRn); a modified pre-fusion respiratory syncvtia virus (RSV) F protein; and a trimerization domain. In an aspect, disclosed are peptides comprising a monomeric Fc fragment of an immunoglobulin recognized by a FcRn; a modified pre-fusion RSV F protein; and a trimerization domain wherein the peptide comprises the sequence:

```
                                              (SEQ ID NO: 1)
mpmgslqplatlyllgmlvasclgQNITEEFYQSTCSAVSKGYLSALRT

GWYTSVITIELSNIKENKCNGTDAKVKLIKQELDKYKNAVTELQLLMQS

TPATNNRARRELPRFMNYTLNNAKKTNVTLSKKRKRRFLGFLLGVGSAI

ASGVAVCKVLHLEGEVNKIKSALLSTNKAVVSLSNGVSVLTFKVLDLKN

YIDKQLLPILNKQSCSISNIETVIEFQQKNNRLLEITREFSVNAGVTTP

VSTYMLTNSELLSLINDMPITNDQKKLMSNNVQIVRQQSYSIMCIIKEE

VLAYVVQLPLYGVIDTPCWKLHTSPLCTTNTKEGSNICLTRTDRGWYCD

NAGSVSFFPQAETCKVQSNRVFCDTMNSLTLPSEVNLCNVDIFNPKYDC

KIMTSKTDVSSSVITSLGAIVSCYGKTKCTASNKNRGIIKTFSNGCDYV

SNKGVDTVSVGNTLYYVNKQEGKSLYVKGEPIINFYDPLVFPSDEFDAS

ISQVNEKINQSLAFIRKSDELLgsgsgsRSLVPRGSPGSGYIPEAPRDG

QAYVRKDGEWVLLSTFLGGSGGGGSGGGGSGSEPRGPTIKPSPPSKSPA

PNLLGGPSVFIFPPPKIKDVLMISLSPIVTCVVVDVSEDDPDVQISWFVN

NVEVHTAQTQTHREDYNSTLRVVSALPIQHQDWMSGKAFACAVNNKDLP

APIERTISKPKGSVRAPQVYVLPPPEEEMTKKQVTLTCMVTDFMPEDIY
```

-continued
```
VEWTNNGKTELNYKNTEPVLDSDGSYFMYSKLRVEKKNWVERNSYSCSV

VHEGLHNHHTTKSFSRTPGK.
```

The lower case letters represent a CD5 signal peptide. The bold, capitalized letters represent a modified pre-fusion RSV F protein containing only the ectodomain of the F protein. The underlined, lower case letters represent a 6 GS linker. The italicized, lower case letters represent a 14 GS linker. The double underlined, capitalized letters represent a thrombin recognition site. The underlined, capitalized letters represent foldon from T4 fibritin. The bold, underlined, capitalized letters represent a mouse Fc IgG2a single chain. The double underlined codons in the Fc IgG2a show the three cysteine sites that are mutated to serine in order to generate a monomeric Fc IgG2a. The two grey highlighted regions of the monomeric Fc IgG2a are regions responsible for FcRn binding. The first sequence, HQ, can be mutated to AD. The second sequence, HN, can be mutated to AQ in order to abolish FcRn binding.

In some instances, disclosed are peptides comprising a monomeric Fc fragment of an immunoglobulin recognized by a FcRn; a modified pre-fusion RSV F protein; and a trimerization domain wherein the peptide comprises a sequence that is 90% identical to the sequence of SEQ ID NO: 1. In an aspect, disclosed are peptides comprising a monomeric Fc fragment of an immunoglobulin recognized by a FcRn; a modified pre-fusion RSV F protein; and a trimerization domain w-herein the peptide comprises a sequence that is 90% identical to the sequence of SEQ ID NO: 1, wherein the CD5 signal peptide, modified pre-fusion RSV F protein containing only the ectodomain of the F protein, the GS linker, the 14 GS linker, the thrombin recognition site, the foldon from T4 fibritin, the mouse Fc IgG2a single chain, or the regions of the monomeric Fc IgG2a regions responsible for FcRn binding are the same or 50%, 55%, 65%, 70%, 75%, 80%, 90%, 95%, 96%, 97%, 98%, or 99% identical to the sequence of SEQ ID NO: 1.

In some instances, disclosed are peptides comprising a monomeric Fc fragment of an immunoglobulin recognized by a FcRn; a modified pre-fusion RSV F protein; and a trimerization domain wherein the peptide comprises a sequence that is 90% identical to the sequence of SEQ ID NO: 1. In an aspect, disclosed are peptides comprising a monomeric Fc fragment of an immunoglobulin recognized by a FcRn; a modified pre-fusion RSV F protein; and a trimerization domain wherein the peptide comprises a sequence that is 90% identical to the sequence of SEQ ID NO: 1, wherein the CD5 signal peptide, modified pre-fusion RSV F protein containing only the ectodomain of the F protein, the GS linker, the 14 GS linker, the thrombin recognition site, the foldon from T4 fibritin, the mouse Fc IgG2a single chain, or the regions of the monomeric Fc IgG2a regions responsible for FcRn binding are deleted or substituted with a different sequence, such as a different monomeric Fc fragment of an immunoglobulin recognized by a FcRn; a different modified pre-fusion RSV F protein; or a different trimerization domain.

Also disclosed are peptides comprising a monomeric Fc fragment of an immunoglobulin recognized by a FcRn; a modified post-fusion RSV F protein; and a trimerization domain.

1. Monomeric Fc fragment of an immunoglobulin recognized by FcRn

A monomeric Fc fragment of an immunoglobulin as disclosed herein can be recognized by a FcRn. In some instances the monomeric Fc fragment of an immunoglobulin comprises a mutation in the Fc region of an immunoglobulin recognized by FcRn sequence that results in the prevention of dimer formation. In some aspects, the monomeric Fc fragment of an immunoglobulin recognized by a FcRn comprises a mutation in cysteine residues responsible for dimer formation.

In some instances, the amino acid sequence of a monomeric Fc fragment of a mouse 1gG2a can be EPRGPTIKPSPPSKPAPNLLGGPSVFIFPPKIKDVLMISLSPIV-TCVVVDVSEDDPDVQIS WFVNNVEVHTAQTQTHREDYNSTLRVVSAL-PiQHQDWMSGKAFACAVNNKDLPAPIE RTISKPKGSVRAPQVYVLPP-PEEEMTKKQVTLTCMVTDFMPEDIYVEWTNNGK-TELNY KNTEPVLDSDGSYFMYSKLRVEK-KNWVERNSYSCSVVHEGLHNHHTTKSFSRTPGK (SEQ ID NO:2) or a sequence 50%, 55%, 65%, 70%, 75%, 80%, 90%, 95%, 96%, 97%, 98%, or 99%/9 identical to the sequence of SEQ ID NO:2. The bold underlined amino acids represent a mutation from cysteine to serine to generate a single chain Fc.

In some instances, the nucleic acid sequence of a monomeric Fc fragment of a mouse IgG2a can be GAGCCCAGAGGGCCCACAATCAAGCCCTCTCCTC-CATCCAAATCCCCAGCACCTAA CCTCTCCCAGGTGGACCATCCGTCTT-CATCTTCCCTCCAAAGATCAACGATGTACTCAT GATCTCCCTGAGCCCCATAGTCA-CATGTGTGGTGGTGGATGTGAGCGAGGATGACC CAGATGTCCAGATCAGCTGGTTTGTAACAACGTG-GAAGTACACACAGCTCAGACA CAAACCCAT-AGAGAGGATTA-CAACAGTACTCTCCGGGTGGTCAGTGCCCTCCCCAT CCAGCACCAGGACTGGAT-GAGTGGCAAGGCGTTCGCATGCGCGGT-CAACAACAAA GACCTCCCAGCGCC-CATCGAGAGAACCATCTCAAAACCCAAAGGGTC-AGTAAGAGC TCCACAGGTATATGTCTGCCTC-CACCAGAAGAAGAGATGACTAAGAAACAGGTCA CTCTGACCTGCATGGTCACAGACTTCATGCCTGAA- GACATACGTGGAGTGGACCA ACAACGG-GAAAACAGAGCTAAACTACAAGAACACT-GAACCAGTCCTGGACTCTGAT GGTTCTTACTTCATGTACAGCAAGCTGAGAGTG-GAAAAGAAGAACTGGGTGGAAAG AAATAGC-TACTCCTGTTCAGTGGTC-CACGAGGGTCTGCACAATCACCACACGACTA AGAGCTTCTCCCGGACTCCGGGTAAA (SEQ ID NO:3) or a sequence 50%, 55%, 65%, 70%, 75%, 80%, 90%, 95%, 96%, 97%, 98%, or 99% identical to the sequence of SEQ ID NO:3. The bold underlined nucleic acids represent a mutation that encodes serine instead of cysteine to generate a single chain Fc.

In some instances, corresponding mutations can be made in other IgG Fc fragments in order to mutate the cysteine residues responsible for dimer formation.

In some instances, other mutations can be made throughout the Fc fragment of an immunoglobulin recognized by a FcRn so long as the FcRn binding region is not affected. For example, in some instances, the amino acid sequence of a monomeric Fc fragment of a mouse IgG2a with FcRn-binding abolished can be EPRGPTIKPSPPSK-SPAPNLLGGPSVFIFPPKIKDVLMISLSPIV-TCVVVDVSEDDPDVQIS WFVNNVEVHTAQTQTHREDYNSTLRVVSAL-PIQADDWMSGKAFACAVNNKDLPAPIE RTISKPKGSVRAPQVYVLPP-PEEEMTKKQVTLTCMVTDFMPEDIYVEWTNNGK-TELNY KNTEPVLDSDGSYFMYSKLRVEK-KNWVERNSYSCSVVHEGLAQHHTTKSFSRTPGK (SEQ ID NO: 4). The bold underlined amino acids represent mutations that generate abolished FcRn-binding.

In some instances, the nucleic acid sequence of a monomeric Fc fragment of a mouse IgG2a with FcRn-binding abolished can be GAGCCCAGAGGGCCCACAAT-CAAGCCCTCTCCTCCATC-CAAATCCCCAGCACCTAA CCTCTTGGGTGGAC-CATCCGTCTCATCTTCCCTCCAAAGATCAAGGATG-TACTCAT GATCTCCCTGAGCCCCATAGTCA-CATGTGTGGTCYGTGGATGTGAGCGAGCGATGACC CAGATGTCCAGATCAGCTGGTTTGTAACAACGTG-GAAGTACACACAGCTCAGACA CAAACCCAT-AGAGAGGATTA-CAACAGTACTCTCCGGGTGGTCAGTGCCCTCCCCAT CCAGGCCGACGACTGGAT-GAGTGGCAAGGCGTTCGCATGCGCGGT-CAACAACAAA GACCTCCCAGCGCC-CATCGAGAGAACCATCTCAAAACCCAAAGGGTCA-GTAAGAGC TCCACAGGTATATGTCTTGCCTC-CACCAGAAGAAGAGATGACTAAGAAACAGGTCA CTCTGACCTGCATGGTCACAGACTTCATGCCTGAA-GACATTTACGTGGAGTGGACCA ACAACGG-GAAAACAGAGCTAAACTACAAGAACACT-GAACCAGTCCTGGACTCTGAT GGTTCTTACTTCATGTACAGCAAGCTGAGAGTG-GAAAAGAAGAACTGGGTGGAAAG AAATAGC-TACTCCTGTTCAGTGGTCCACGAGGGTCTGGCC-AACACCACACGACTA AGAGCTTCTCCCCJGACTCCGGGTAAA (SEQ ID NO:5) or a sequence 50%, 55%, 65%4, 70%, 75%, 80%, 90%, 95%, 96%, 97%, 98%, or 99% identical to the sequence of SEQ ID NO:5. The bold underlined nucleic acids represent mutations that generate abolished FcRn-binding.

In some instances, the monomeric Fc fragment of an immunoglobulin recognized by a FcRn is conjugated to the carboxy terminal end of the pre-fusion RSV F protein. The conjugation can be direct or indirect. Indirect conjugation can be due to the presence of a linker in between the modified pre-fusion RSV F protein and the monomeric Fc fragment of an immunoglobulin recognized by a FcRn.

In some instances, the monomeric Fc fragment of an immunoglobulin recognized by a FcRn is an IgG Fc fragment.

2. Modified Pre-Fusion RSV F Protein

In some instances, a modified pre-fusion RSV F protein is a variant of the wild type sequence of pre-fusion RSV F protein that allows the protein to be soluble. For example, the wild type sequence of pre-fusion RSV F protein can be MELLILKANAITTILTAVTFCFASGQNI-TEEFYQSTCSAVSKGYLSALRTGWYTSVITIELS NIKENKCNGTDAKVKLIKQELDKYKNAVTELQLL-MQSTPPTNNRARRELPRFMNYTLN NAKKTNVTL-SKKRKRRFLGFLLGVGSAIASGVAVSKVLHLE-GEVNKIKSALLSTNKAV VSLSNGVSVLTSKVLDLKNYIDKQLLPIVNKQSCSIS-NIETVIEFQQKNNRLLEITREFSVN AGVTTPVSTYMLTN- SELLSLINDMPITNDQKKLMSNNVQIVRQQSYSIM-
SIIKEEVLAYV VQLPLYGVIDTPCWKLHT-
SPLCTTNTKEGSNICLTRTDRGWYCDNAGSVSFFPQ-
AETCK VQSNRVFCDTMNSLTLPSEINLCNVDIFNP-
KYDCKIMTSKTDVSSSVITSLGAIVSCYGKT
KCTASNKNRGIIKTFSNGCDYVSNKGMDTVSVGNT-
LYYVNKQEGKSLYVKGEPIINFY DPLVFPSDEFDA-
SISQVNEKINQSLAFIRKSDELLHNVNAGKSTTNIMIT-
TIIIVIIVILLSLI
AVGLLLYCKARSTPVTLSKDQLSGINNIAFSN (SEQ ID NO:6) or a sequence 50%, 55%, 65%, 70%, 75%, 80%, 90%, 95%, 96%, 97%, 98%, or 998% identical to the sequence of SEQ ID NO:6. Thus, any mutations to SEQ ID NO:6 that result in a soluble form of pre-fusion RSV F protein can be considered a modified pre-fusion RSV F protein.

In some instances, a modified pre-fusion RSV F protein can lack the signaling peptide present in amino acids 1-25 of wild type RSV F protein.

In some instances, a modified pre-fusion RSV F protein contains only the ectodomain of wild type RSV F protein. In some instances, four point mutations, S155C, S190F, V207L, and S290C (as compared to SEQ ID NO: 6) are present in the modified pre-fusion RSV F protein in order to help maintain the pre-fusion structure.

For example, the amino acid sequence of the ectodomain of RSV F protein can be QNITEEFYQSTCSAVSKGYL-
SALRTGWYTSVITIELSNIKENKCNGTDAKVK-
LIKQELDK YKNAVTELQLLMQSTPATNNRARREL-
PRFMNYTLNNAKKTNVTLSKKRKRRFLGFLLG
VGSAIASGVAVJKVLHLEGEVNKIKSALL-
STNKAVVSLSNGVSVLTEKVLDLKNYIDK
QLLPILNKQSCSISNIETVIEFQQKNNRLLEITRE-
FSVNAGVTTPVSTYMLTNSELLSLIND
MPITNDQKKLMSNNVQIVRQQSYSIMCIIKEEVLAY-
VVQLPLYGVIDTPCWKLHTSPLC TTNTKEGSNICL-
TRTDRGWYCD-
NAGSVSFFPQAETCKVQSNRVFCDTMNSLTLPSEVNL
CNVDIFNPKYDCKIMTSKTDVSSSVITSLC-
GAIVSCYGKTKCTASNKNRGIIKTFSNGCDY
VSNKGVDTVSVGNTLYYVNKQEGKSLYVKGEPI-
INFYDPLVFPSDEFDASISQVNEKINQ SLAFIRKS-
DELL (SEQ ID NO:7). The bold underlined amino acids represent four mutations—S155C; SI90F; V207L. and S290C. The position numbers are based on amino acids 1-25 being present and starting with amino acid 26 which is the beginning of the ectodomain. The amino acid sequence of the ectodomain of RSV F protein can be 50%, 55%, 65%, 70%, 75%, 80%, 90%, 95%, 96%, 97%, 98%, or 99% identical to the sequence of SEQ ID NO: 7.

In some instances, the nucleic acid sequence that encodes the ectodomain of RSV F protein can be CAGAACAT-
CACCGAGGAATTC-
TACCAGAGCACCTGCAGCGCCGT-
GAGCAAGGGCTA
CCTGAGCGCCCTGCGGACCGGCTGGTA-
CACCAGCGTGATCACCATCGAGCTGTCCA ACAT-
CAAAGAAAACAAGTGCAACGGCACCGACGC-
CAAAGTGAAGCTGATCAAGCA
GGAACTGGACAAGTA-
CAAGAACGCCGTGACCGAGCTGCAGCTGCT-
GATGCAGAGC ACCCCCGCCAC-
CAACAACAGAGCCAGAAGAGAGCTGCCCCGGTTCAT-
GAACTACAC
CCTGAACAACGCCAAGAAAACCAACGTGACCCT-
GAGCAAGAAGAGAAAGAGAAGA
TTCCTGGGCITCCTGCTGGGCGTGGGCAGCGCCAT-
TGCCAGCGGCGTGGCCGTGTGT
AAAGTGCTGCACCTGGAAGGCGAAGTGAACAA-
GATCAAGTCCGCCCTGCTGTCCAC
CAACAAGGCCGTGGTGTCCCTGAGCAACGGCGT-
GAGCGTICTGACCTTCAAGGTGC TGGATCT-
GAAGAACTACATCGACAAGCAGCTGCTGCC-
CATCCTGAACAAGCAGAGC
TGCAGCATCAGCAACATCGAGACAGT-
GATCGAGTTCCAGCAGAAGAACAACCGGCT GCTG-
GAAATCACCCGGGAGTTCAGCGT-
GAACGCCGCGAGTGACCACCCCCGTGTCCA
CCTACATGCTGAcCAACAGCGAGCTGCTGTCCCT-
GATCAATGACATGCCCATCACCA
ACGACCAGAAAAAGCTGATGAGCAACAACGTGCA-
GATCGTGCGGCAGCAGAgCTAC agCaTCATGTGCAT-
CATCAAAGAAGAGgTGCTGGCC-
TACGTGGtGCAGCTGCCCCTGtA
CGGCgtgATCGACAcCCCCTGCTG-
GaAGCTGCACACCAGcCCCCtGTGCACAACCAACA
CCAAAGAGGGCAGCAA-
CATcTgcctGACCCGGACCGACCGGGGCtGGTACTG-
CGACAA CGCCGGCAGCTGTCTTTcTTC-
CACAGGCCGAGACATGCAAGGTGCAGAGCAACC
GGGTGTTcTGCGACACCAT-
GAACAGCCTGACCcTGCCCTCcGAAGTGAACC-
TOTCCA ACGTGGACATCITCAACCC-
CAAGTACGACTGCAAGATCATGACCTCCAAGACC-
GAC GTGTCCAGCTCCGTGAT-
CACCTCCCTGGGCGCCATCGTGTCCTGC-
TACGGCAAGACC
AAGTGCACCGCCAGCAACAAGAACAGAGGCAT-
CATCAAGACCTTCAGCAACGGCT GCGAC-
TACGTGTC-
CAATAAGGGCGTGGACACCGTGTCCGTGGGCAA-
CACACTGTAC TACGTGAATAAGCAG-
GAAGGCAAGAGCCTGTACGTGAAGGGCGAGCC-
CATCATCA ACTTC-
TACGACCCCCTGGTGTTCCCCAGCGACGAGTTCG-
ACGCCAGCATCAGCCAG GTGAACGAGAAGAT-
CAACCAGAGCCTGGCCTT-
CATCAGAAAGAGCGACCGAACTGCT G (SEQ ID NO:8) or a sequence 50%, 55%, 65%, 70%, 75%, 80%, 90%, 95%, 96%, 97%, 98%, or 99% identical to the sequence of SEQ ID NO:8. The codons encoding for the four point mutations. S155C. S190F, V207L, and S290C, are underlined.

In some instances, a modified pre-fusion RSV F protein can be mutated in the transmembrane domain. For example, the transmembrane domain of SEQ ID NO:6 is amino acids 530-550 and therefore, a mutation within the transmembrane domain that leads to a soluble pre-fusion RSV F protein is a modified pre-fusion RSV F protein. In some instances, the entire transmembrane domain is absent from the modified pre-fusion RSV F protein.

In some instances, a modified pre-fusion RSV F protein can be further mutated in the cytoplasmic tail. For example, the cytoplasmic tail of SEQ ID NO:6 is amino acids 551-574 and therefore, a mutation within the cytoplasmic tail that leads to a soluble pre-fusion RSV F protein is a modified pre-fusion RSV F protein. In some instances, the entire cytoplasmic tail is absent from the modified pre-fusion RSV F protein.

3. Trimerization Domain

The disclosed peptides have a trimerization domain. In some instances, the trimerization domain is a T4 fibritin trimerization domain. For example, the T4 fibritin trimerization domain can be foldon. In some instances, the amino acid sequence of foldon is GSGYIPEAPRDGQAY- VRKDGEWVLLSTFL (SEQ ID NO:9). In some instances, the amino acid sequence of foldon is 50%, 55%, 65%, 70%, 75%, 80%, 90%, 95%, 96%, 97%, 98%, or 99% identical to SEQ ID NO: 9. For example, the nucleic acid sequence of foldon can be represented by the sequence GGCAGCGGC-TACATCCCCGAGGCCCCAGAGACGGCCAGGCC-TACGTGAGAAAGG ACGGCGAGTGGGTGCTGCT-GAGCACCTTCCTG (SEQ ID NO:10).

In some instances, the trimerization domain can be, but is not limited to the transcription factor GCN4pII trimerization motif (MKQIEDKIEEILSKIYHIENEIARIKKLIGEV; SEQ ID NO: 11), or human collagen XV trimerization domain. In some instances, the trimerization domain can be an amino acid sequence that is 50%, 55%, 65%, 70%, 75%, 800, 9%, 95%, 96%, 97%, 98% or 99% identical to SEQ ID NO:11.

4. Linkers

Disclosed are peptides comprising a monomeric Fc fragment of an immunoglobulin recognized by FcRn; a modified pre-fusion respiratory syncytia virus (RSV) F protein; and a trimerization domain further comprising one or more linkers.

In some instances, at least one of the one or more linkers is on the N-terminus end of the monomeric Fc fragment of an immunoglobulin recognized by a FcRn. In some instances, at least one of the one or more linkers is on the C-terminus end of the monomeric Fc fragment of an immunoglobulin recognized by a FcRn.

In some instances, the one or more linkers are small, nonpolar, amino acid linkers. For example, the linker can be a GS-linker. The number of glycine, serine, and glycine/serine repeats can vary in the one or more linkers. Examples of GS linkers can be GSGSGS (SEQ ID NO:12) and GSGGGGSGGGGSGS (SEQ ID NO:13).

5. Additional Elements

In some instances, the disclosed peptides can further comprise cleavage sites or tag sequences.

In some instances, a cleavage site can be present in the disclosed peptides. Cleavage sites can allow for cleavage of the monomeric Fc fragment of an immunoglobulin recognized by FcRn away from the modified RSV F protein. In some instances, a cleavage site can be recognized by a protease or a chemical compound. In some instances, a cleavage site can be a site recognized by, but not limited to, enterokinase, pepsin, factor Xa, tobacco etch virus protease, or thrombin.

In some instances, a tag sequence can be present in the disclosed peptides. In some instances, a tag sequence can be a detection labels/label sequence or a purification tag. As used herein, a detection label or label sequence is any molecule that can be associated with a nucleic acid or peptide, directly or indirectly, and which results in a measurable, detectable signal, either directly or indirectly. Many such labels for incorporation into nucleic acids or coupling to nucleic acid or antibody probes are known to those of skill in the art. Examples of detection labels suitable for use in RCA are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are; FITC (490 nm; 520 nm), Cy3 (554 nm; 568 nm). Cy3.5 (581 nm; 588 nm), Cy5 (652 nm; 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics. Cleveland, Ohio.

In some instances, a label sequence can be, but is not limited to, an isotope marker, colorimetric biosensors, or fluorescent labels. For example, fluorescent markers can be, but are not limited to, green fluorescent protein (GFP) or rhodamine fluorescent protein (RFP). Other label sequences can include biotin, streptavidin, horseradish peroxidase, or luciferase.

In some instances, a tag sequence can be a purification tag. In some instances, a purification tag can be, but is not limited to, histidine, glutathione-S-transferase, albumin-binding protein, FLAG epitope, galactose-binding protein, myc, or hemagglutinin.

6. Modified Post-Fusion RSV F Protein

Also disclosed are peptides comprising a monomeric Fc fragment of an immunoglobulin recognized by a FcRn; a modified post-fusion RSV F protein; and a trimerization domain. In some instances, the peptides comprising a modified post-fusion RSV F protein are identical to the disclosed peptides comprising a modified pre-fusion RSV F protein except for the replacement of the modified pre-fusion RSV F protein with a modified post-fusion RSV F protein. The modifications to the post-fusion RSV F protein can be similar to the pre-fusion protein except that the post-fusion RSV F protein does not contain the four point mutations at positions 155, 190, 207, and 290 (as compared to SEQ ID NO: 6).

In some instances, a modified post-fusion RSV F protein can have mutations in both the transmembrane domain and the cytoplasmic tail. For example, like the modified pre-fusion RSV F protein, the modified post-fusion RSV F protein can have the entire transmembrane domain or cytoplasmic tail deleted. In some instances, mutations are made in the transmembrane domain which result in a soluble post-fusion RSV F protein.

C. Compositions

Disclosed are compositions comprising any of the disclosed peptides. In some instances, disclosed are compositions comprising a monomeric Fc fragment of an immunoglobulin recognized by a FcRn; a modified pre-fusion RSV F protein; and a trimerization domain.

In some instances, the composition can be a vaccine.

In some instances, the compositions can further comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles. e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

The disclosed peptides can be formulated and/or administered in or with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Thus, the compositions disclosed herein can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subject's lung cells. Regarding liposomes, see, e.g., Brigham et al. Am. J. Resp. Cell. Mol. Biol. 1:95 100 (1989); Feigner et al. Proc. Natl. Acad. Sci USA 84:7413 7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In some instances, disclosed are pharmaceutical compositions comprising any of the disclosed peptides described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides described herein and can also include a carrier such as a pharmaceutically acceptable carrier. For example, disclosed are pharmaceutical compositions, comprising the peptides disclosed herein, and a pharmaceutically acceptable carrier. In one aspect, disclosed are pharmaceutical compositions comprising the disclosed peptides. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for nasal, oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In practice, the peptides described herein, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

By "pharmaceutically acceptable" is meant a material or carrier that would be selected to minimize any degradation of the active ingredient and to minimize any adverse side effects in the subject, as would be well known to one of skill in the art. The peptides described herein, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other examples of carriers include dimyristoylphosphatidyl (DMPC), phosphate buffered saline or a multivesicular liposome. For example, PG:PC:Cholesterol: peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa, 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also, co-solvents such as alcohols may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Because of the ease in administration, oral administration can be used, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a disclosed peptide (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. Typically, the final injectable form should be sterile and should be effectively fluid for easy syringability. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Formulations for optical administration may include ointments, lotions, creams, gels, drops, suppositories, sprays, liquids and powders. Conventional pharmaceutical carriers, aqueous, powder or oily bases, thickeners and the like may be desirable.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a disclosed peptide, and/or pharmaceutically acceptable salts thereof, can also be prepared in powder or liquid concentrate form.

The exact dosage and frequency of administration depends on the particular disclosed peptide, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

D. Nucleic Acid Sequences

As this specification discusses various peptide sequences it is understood that the nucleic acids that can encode those polypeptide sequences are also disclosed. This would include all degenerate sequences related to a specific poly peptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

Disclosed are nucleic acid sequences capable of encoding any of the peptides disclosed herein. Further disclosed are nucleic acid constructs comprising the nucleic acid sequences capable of encoding any of the peptides disclosed herein.

For example, SEQ ID NO:14 provides a nucleic acid sequence capable of encoding a peptide comprising a monomeric Fc fragment of an immunoglobulin recognized by FcRn; a modified pre-fusion RSV F protein; and a trimerization domain.

(SEQ ID NO: 14)
atgcccatggggtctctgcaaccgctggccaccttgtacctgctgggga tgctggtcgcttcctgcctcggaCAGAACATCACCGAGGAATTCTACCA

GAGCACCTGCAGCGCCGTGAGCAAGGGCTACCTGAGCGCCCTGCGGACC

GGCTGGTACACCAGCGTGATCACCATCGAGCTGTCCAACATCAAAGAAA

ACAAGTGCAACGGCACCGACGCCAAAGTGAAGCTGATCAAGCAGGAACT

GGACAAGTACAAGAACGCCGTGACCGAGCTGCAGCTGCTGATGCAGAGC

ACCCCCGCCACCAACAACAGAGCCAGAAGAGAGCTGCCCCGGTTCATGA

ACTACACCCTGAACAACGCCAAGAAAACCAACGTGACCCTGAGCAAGAA

GAGAAAGAGAAGATTCCTGGGCTTCCTGCTGGGCGTGGGCAGCGCCATT

GCCAGCGGCGTGGCCGTGTGTAAAGTGCTGCACCTGGAAGGCGAAGTGA

ACAAGATCAAGTCCGCCCTGCTGTCCACCAACAAGGCCGTGGTGTCCCT

GAGCAACGGCGTGAGCGTGCTGACCTTCAAGGTGCTGGATCTGAAGAAC

TACATCGACAAGCAGCTGCTGCCCATCCTGAACAAGCAGAGCGCAGCA

TCAGCAACATCGAGACAGTGATCGAGTTCCAGCAGAAGAACAACCGGCT

GCTGGAAATCACCCGGGAGTTCAGCGTGAACGCCGGAGTGACCACCCCC

GTGTCCACCTACATGCTGAcCAACAGCGAGCTGCTGTCCCTGATCAATG

ACATGCCCATCACCAACGACCAGAAAAAGCTGATGAGCAACAACGTGCA

GATCGTGCGGCAGCAGAgCTACagCaTCATGTGCATCATCAAAGAAGAG gTGCTGGCCTACGTGGtGCAGCTGCCCCTGtACGGCgtgATCGACAcCC CCTGCTGGaAGCTGCACACCAGcCCCtGTGCACAACCAACACCAAAGA GGGCAGCAACATcTgcctGACCCGGACCGACCGGGGCtGGTACTGCGAC AACGCCGGCAGCGTGTCTTTcTTTCCACAGGCCGAGACATGCAAGGTGC AGAGCAACCGGGTGTTcTGCGACACCATGAACAGCCTGACCcTGCCCTC cGAAGTGAACCTGTGCAACGTGGACATCTTCAACCCCAAGTACGACTGC

AAGATCATGACCTCCAAGACCGACGTGTCCAGCTCCGTGATCACCTCCC

TGGGCGCCATCGTGTCCTGCTACGGCAAGACCAAGTGCACCGCCAGCAA

CAAGAACGAGGCATCATCAAGACCTTCAGCAACGGCTGCGACTACGTG

TCCAATAAGGGCGTGGACACCGTGTCCGTGGGCAACACACTGTACTACG

TGAATAAGCAGGAAGGCAAGAGCCTGTACGTGAAGGGCGAGCCCATCAT

CAACTTCTACGACCCCCTGGTGTTCCCCAGCGACGAGTTCGACGCCAGC

ATCAGCCAGGTGAACGAGAAGATCAACCAGAGCCTGGCCTTCATCAGAA

AGAGCGACGAACTGCTGggatcaggctcaggatcaAGAAGC<u>CTGGTGCC</u>

<u>CAGAGGCAGC</u>CCCGGCAGCGGCTACATCCCCGAGGCCCCAGAGACGGC

CAGGCCTACGTGAGAAAGGACGGCGAGTGGGTGCTGCTGAGCACCTTCC

TGGGC<u>ggatcaggcggggtgggtccggaggaggtggctcgggatct</u>GA

GCCCAGAGGGCCCACAATCAAGCCCTCTCCTCCATCCAAATCCCCAGCA

CCTAACCTCTTGGGTGGACCATCCGTCTTCATCTTCCCTCCAAAGATCA

AGGATGTACTCATGATCTCCCTGAGCCCCATAGTCACATGTGTGGTGGT

GGATGTGAGCGAGGATGACCCAGATGTCCAGATCAGCTGGTTTGTGAAC

AACGTGGAAGTACACACAGCTCAGACACAAACCCATAGAGAGGATTACA

ACAGTACTCTCCGGGTGGTCAGTGCCCTCCCCATCCAGC<s>ACCAG</s>GACTG

GATGAGTGGCAAGGCGTTCGCATGCGCGGTCAACAACAAAGACCTCCCA

GCGCCCATCGAGAGAACCATCTCAAAACCCAAAGGGTCAGTAAGAGCTC

CACAGGTATATGTCTTGCCTCCACCAGAAGAAGAGATGACTAAGAAACA

GGTCACTCTGACCTGCATGGTCACAGACTTCATGCCTGAAGACATTTAC

GTGGAGTGGACCAACAACGGGAAAACAGAGCTAAACTACAAGAACACTG

AACCAGTCCTGGACTCTGATGGTTCTTACTTCATGTACAGCAAGCTGAG

AGTGGAAAAGAAGAACTGGGTGGAAAGAAATAGCTACTCCTGTTCAGTG

<u>GTCCACGAGGGTCTG</u><s>ACAAT</s>CACCACACGACTAAGAGCTTCTCCCGGA

CTCCGGGTAAATAA, or a sequence 50%, 55%, 65%, 70%, 75%, 80%, 90%, 95%, 96%, 97%, 98%, or 99%, identical to the sequence of SEQ ID NO:14. The lower case letters represent a CD5 signal peptide. The bold, capitalized letters represent a modified pre-fusion RSV F protein containing only the ectodomain of the F protein. The underlined, lower case letters represent a 6 GS linker. The italicized, lower case letters represent a 14 GS linker. The double underlined, capitalized letters represent a thrombin recognition site. The underlined, capitalized letters represent foldon from T4 fibritin. The bold, underlined, capitalized letters represent a mouse Fc IgG2a single chain. The double underlined codons in the Fe IgG2a show the three cysteine sites that are mutated to serine in order to generate a monomeric Fc IgG2a. The dotted underlined, capitalized letters at the end of the sequence represent a stop codon. The two grey highlighted regions of the monomeric Fc IgG2a are regions responsible for FcRn binding. In an aspect, the first sequence, CACCAG, can be mutated to GCCGAC. In an aspect, the second sequence. CACAAT, can be mutated to GCCCAA in order to abolish FcRn binding.

Disclosed are vectors comprising a nucleic acid sequence capable of encoding peptides comprising a monomeric Fc fragment of an immunoglobulin recognized by a neonatal receptor (FcRn); a modified pre-fusion respiratory syncytia virus (RSV) F protein; and a trimerization domain. In some instances, the peptide can be any of the peptides disclosed herein.

In some instances, the disclosed vectors can further comprise a nucleic acid sequence capable of encoding a tag (e.g. label or purification tag). In some aspects, the label can be any peptide or protein that is encoded for by a nucleic acid. For example, the labeling moiety can be, but is not limited to, GST, myc, His. or GFP.

In some instances, the labeling moiety can be operably linked to the nucleic acid sequence capable of encoding the peptides comprising a monomeric Fc fragment of an immunoglobulin recognized by a neonatal receptor (FcRn): a modified pre-fusion respiratory syncytia virus (RSV) F protein; and a trimerization domain. Thus, the labeling moiety and the peptide can be transcribed together.

In addition to a nucleic acid sequence capable of encoding the disclosed peptides, the disclosed vectors can carry regulatory sequences that control the expression of the disclosed peptides in a host cell. It will be appreciated by those skilled in the art that the design of the vector, including the selection of regulatory sequences can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods of expressing polypeptides in bacterial cells or fungal cells, e.g., yeast cells, are also well known in the art.

In some instances, the disclosed vectors further comprise a promoter operably linked to the nucleic acid sequence capable of encoding the disclosed peptides. In some instances, the promoter can be an inducible promoter. In some instances, the promoter can be a cell-specific promoter. The nucleic acid sequence capable of encoding the disclosed peptides can be functionally linked to a promoter. By "functionally linked" is meant such that the promoter can promote expression of the nucleic acid sequence, thus having appropriate orientation of the promoter relative to the nucleic acid sequence.

E. Methods

Disclosed are methods for eliciting a protective immune response against RSV comprising administering to a subject an effective amount of a composition comprising any of the peptides, nucleic acids or vectors disclosed herein.

Disclosed are methods for eliciting a protective immune response against RSV comprising administering to a subject an effective amount of a composition comprising a monomeric Fc fragment of an immunoglobulin recognized by FcRn; a modified pre-fusion RSV F protein; and a trimerization domain, wherein the administering is to a mucosal epithelium.

In some instances, the mucosal epithelium is selected from the group consisting of: lungs, intestines, trachea, colon, nasal tissue, and vaginal tissue.

In some instances, administering is intranasal administering. In some instances, any form of administering that allows for delivery to a mucosal epithelium can be used.

In some instances, an adjuvant is further administered with the composition. In some instances, an adjuvant can be formulated with the peptide into the disclosed compositions. Thus, the adjuvant can be administered simultaneously with the peptide. In some instances, the adjuvant is separate from the disclosed compositions and therefore can be administered simultaneously with the composition or separate from the composition. The adjuvant can be, for example, but is not limited to, CpG, MPL, poly[di(sodium carboxylatoethylphenoxy)phosphazene] (PCEP), poly[di(sodium carboxylatophenoxy)phosphazene] (PCPP), the Cholera Toxin-Derived CTA1-DD, Flagellin, IDRI1002. α-Galactosylceramide, or saponins.

In some instances, the protective immune response elicited is the production of antibodies directed to the pre-fusion RSV F protein.

Disclosed are methods of treating a subject exposed to RSV or at risk of being exposed to RSV comprising administering to the subject an effective amount of a composition comprising a monomeric Fc fragment of an immunoglobulin recognized by FcRn; a modified pre-fusion RSV F protein; and a trimerization domain, wherein the administering is to a mucosal epithelium. In some instances, any of the disclosed peptides can be administered a part of a composition or pharmaceutical composition to the subject for treatment.

F. Combination Therapy

In one aspect of the disclosed methods, the compositions can be administered alone or in combination with one or more additional therapeutic agents. The additional therapeutic agents are selected based on the disease or symptom to be treated. A description of the various classes of suitable pharmacological agents and drugs may be found in Goodman and Gilman, The Pharmacological Basis of Therapeutics, (11 th Ed., McGraw-Hill Publishing Co.) (2005).

G. Kits

The compositions and materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the disclosed peptides, the kit comprising monomeric Fc fragment of an immunoglobulin recognized by a.FcRn and a modified pre-fusion RSV F protein. The kits also can contain vectors.

EXAMPLES

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

A. Example 1

Figures 3A, 3B, 3C:
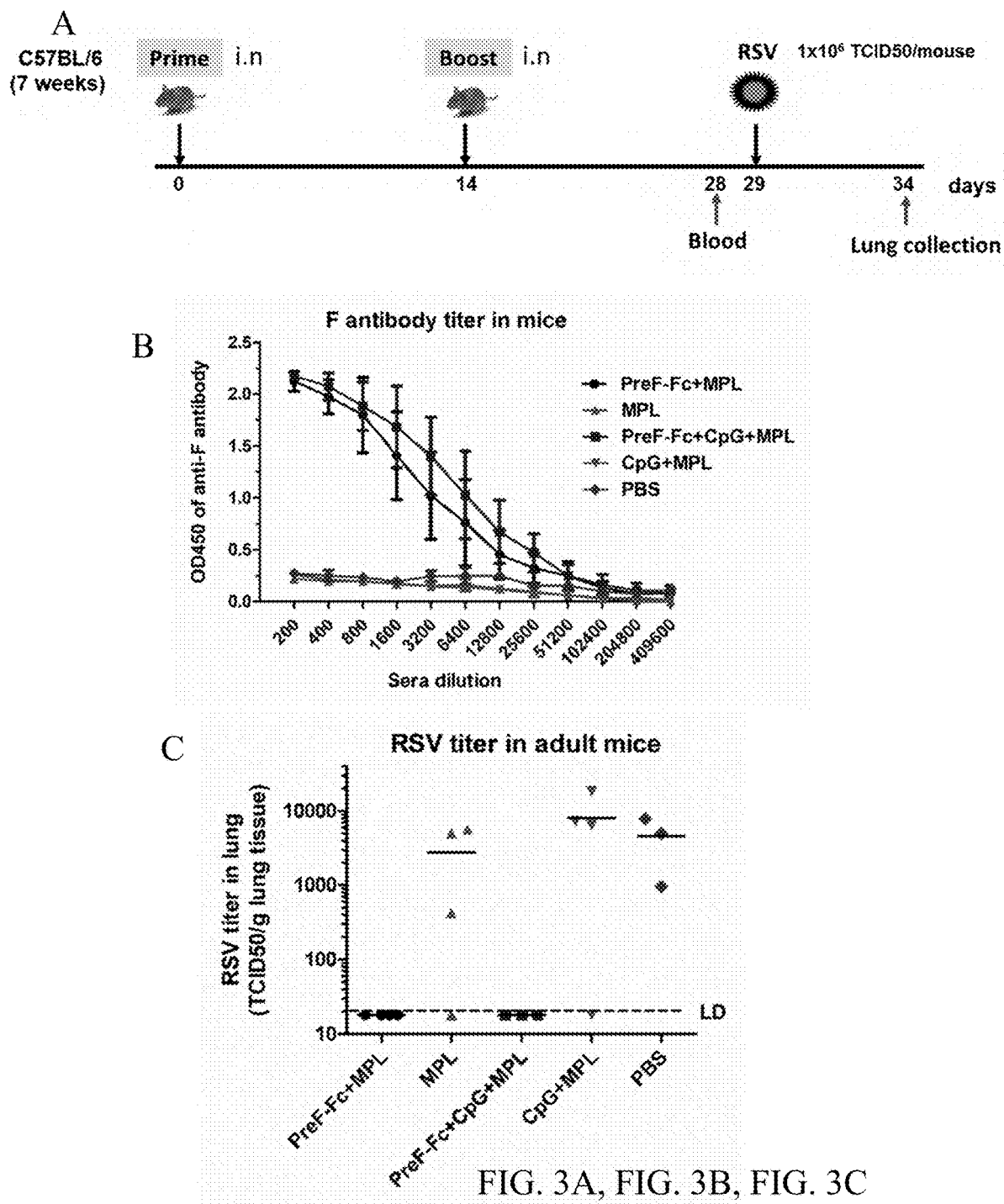
FIGS. 3A, 3B, and 3C show an experimental design in mice. A) outline of the experiment; B) RSV F antibody titer; C) RSV titer.

FIG. 3A shows a schematic diagram showing the immunization procedure of Fc-fused PreF protein. The C57BL6 (7-week old) were intranasally immunized twice at two-week intervals with the Fc-fused PreF protein and adjuvants. The mice were bled at day 14 after boost to harvest sera for antibody test. Then the mice were challenged with RSV-A2 strain. The lungs were collected at day 5 post-challenge for virus titration. (FIG. 3B). RSV F specific antibody responses were determined in different groups. Briefly, the mice were immunized with PreF-Fc protein (10 µg) along with MPL (10 µg) and/or CpG (5 µg). The mice administrated with adjuvants alone or PBS serve as the negative control. An ELISA assay was used to detect antibody titers in the serially-diluted mouse sera. FIG. 3C shows the RSV titer in mouse lungs. At day 5 post-infection, the individual lungs were collected and virus titers (TCID50/ml) were determined using the method of Reed and Muench.

B. Example 2

RSV infects the lungs and airways of humans and is known for global prevalence. Healthy people usually have mild, cold-like symptoms and recover in a week or two. However, severe infections, especially in infants and older adults can lead to mortality. Virtually all infants or older adults can be potentially infected with RSV and 1-2%, or more, of all infected children or older adults, require intensive care in a hospital, with RSV infection in children implicated in asthma development. It is believed that in the US alone, RSV infection annually accounts for the hospitalization of more than 57,000 children younger than 5 years old and the deaths of about 14,000 adults older than 65 years. A formalin-inactivated (FI) RSV vaccine developed in the 1960's caused augmented disease and increased mortality among some of the infant vaccine recipients upon a subsequent natural RSV infection. The underlying mechanisms of the RSV FI vaccine-enhanced disease remain elusive. Despite the significant health and economic burden, there is currently no approved RSV vaccine on the global market. An ideal RSV vaccine not only blocks virus growth but also avoids vaccine-associated disease. Therefore, there is an urgent need for developing an effective and safe RSV vaccine suitable for all age groups.

Figure 4:
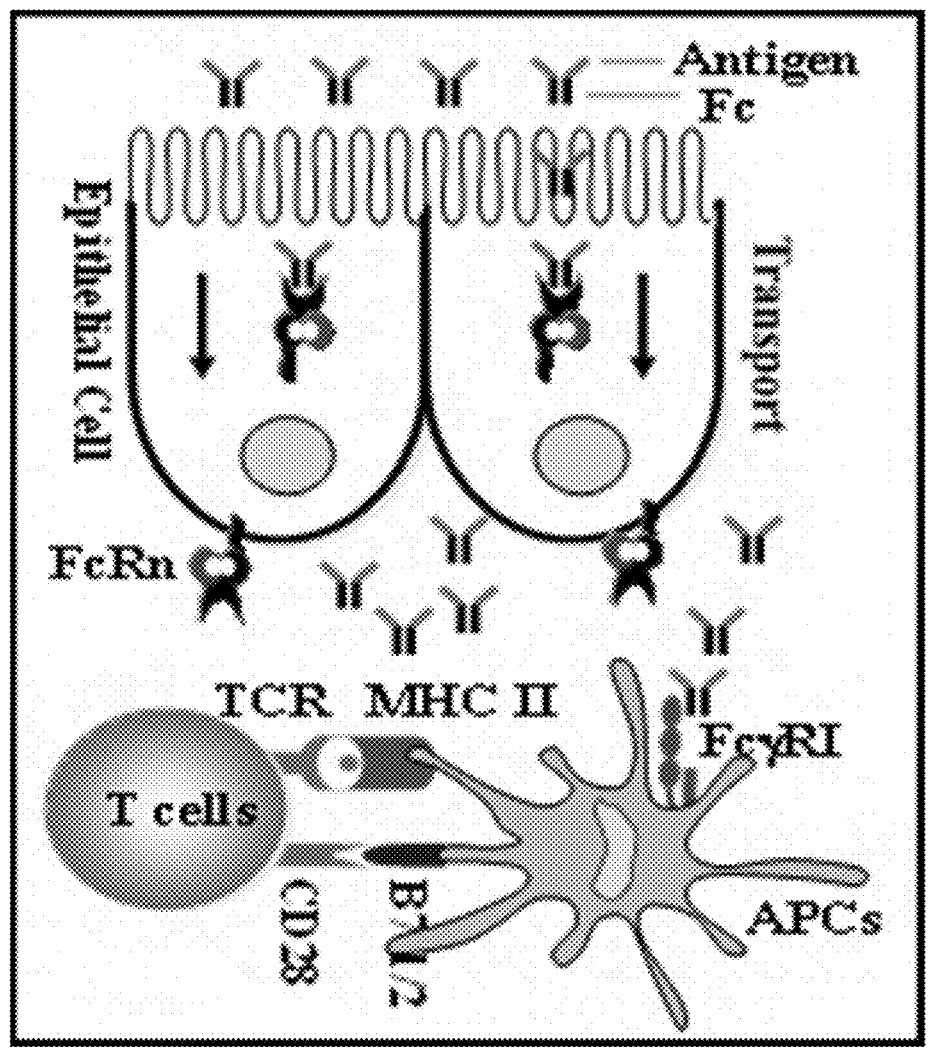
FIG. 4 shows a proposed model of FcRn-mediated vaccine antigen transport across epithelial barrier to target to mucosal antigen presenting cells, activate T cells.

The current disclosure takes advantage of the properties of the neonatal Fc receptor (FcRn), which recognizes the Fc portion of immunoglobulin G (IgG) and transports these antibodies across mucosal surfaces. The technology involves fusing an antigen to the Fc moiety of human IgG, which then binds to FcRn, thus transporting the antigen across the mucosal barrier (FIG. 4). This technology has characteristics of a "platform technology" in that construction of these antigenic fusions, their manufacture and purification are consistent across many target antigens using many established, pharmaceutical-friendly production systems (upstream production in CHO cells using protein A downstream). FcRn targeted intranasal delivery of an RSV vaccine antigen potentially offers significant advantages in terms of safety and efficacy, over the RSV vaccines currently in development. Another advantage of FcRn targeted RSV mucosal vaccine is effective immunity in the lung something conventional vaccines delivered via intramuscular injections (IM) are incapable of delivering. Vaccines that can induce lung immunity to RSV are likely to be more effective because an immune barrier is created at the port of entry before RSV can establish itself and multiply The current disclosure determines the ability of the FcRn platform to deliver an RSV subunit vaccine F antigen across the respiratory mucosal barrier to engender protective immune responses against RSV infection in mice that faithfully mimic the human disease. FcRn-mediated respiratory immunizations can be a novel and valuable platform for the development of a safe and effective RSV vaccine. The current data showed that mice immunized intranasally (i.n.) by the PreF-Fc protein produced a high level of F-specific IgG antibody response in the sera (FIG. 3B). After mice were i.n, challenged with RSV, highest lung viral loads were detected in the adjuvant alone or PBS groups, on the contrary, the virus was barely detected in PreF-Fc-immunized mice (FIG. 3C). Overall, the mice immunized by the PreF-Fc proteins shows protection from RSV infection, although these preliminary data needs to be verified in more animal studies and by histopathology analysis.

The PreF-Fc protein used in these studies is a peptide comprising a monomeric Fc fragment of IgG (an immunoglobulin recognized by a FcRn); a modified pre-fusion RSV F protein; and a trimerization domain.

Those skilled in the art will recognize, or be able to ascertain using no more than routine experimentation, many equivalents to the specific embodiments of the method and compositions described herein. Such equivalents are intended to be encompassed by the following claims.

1. Allie S R, Randall T D. Pulmonary immunity to viruses. Clin Sci (Lond), 2017 Jun. 30; 131(14):1737-1762.
2. Berneman A, Belec L, Fischetti V A, Bouvet J P, 1998. The specificity patterns of human immunoglobulin G antibodies in serum differ from those in autologous secretions. Infect Immun. 66:4163-4168.
3. Boukhvalova M S, Blanco J C. 2013. The cotton rat Sigmodon hispidus model of respiratory syncytial virus infection. Curr Top Microbiol Immunol. 372:347-58.
4. Castilow E M, Varga S M. 2008. Overcoming T cell-mediated immunopathology to achieve safe RSV vaccination. Future Virol. 3:445-454.
5. Cullen L M, Blanco J C, Morrison T G. 2015. Cotton rat immune responses to virus-like particles containing the pre-fusion form of respiratory syncytial virus fusion protein. J Transl Med. 13:350.
6. Garg R, Latimer L, Simko E, Gerdts V, Potter A, van den Hurk Sv. Induction of mucosal immunity and protection by intranasal immunization with a respiratory syncytial virus subunit vaccine formulation. J Gen Virol. 2014 February; 95(Pt 2):301-6.
7. Garg R, Theaker M, Martinez E C, van Drunen Littel-van den Hurk S. A single intranasal immunization with a subunit vaccine formulation induces higher mucosal IgA production than live respiratory syncytial virus. Virology. 2016 December; 499:288-297.
8. Gebril A. Alsaadi M, Acevedo R, Mullen A B, Ferro V A. 2012. Optimizing efficacy of mucosal vaccines. Expert Rev Vaccines. 11:1139-55.
9. Graham B S, Modjarrad K, McLellan J S. 2015. Novel antigens for RSV vaccines. Curr Opin Immunol. 35:30-8.
10. Holmgren J, Svennerholm A M. 2012. Vaccines against mucosal infections. Curr Opin Immunol. 24:343-53.
11. Joyce M G, Zhang B, Ou L, Chen M, Chuang G Y, Druz A, Kong W P, Lai Y T, Rundlet E J, Tsybovsky Y, Yang Y, Georgiev I S, Guttman M, Lees C R, Pancera M, Sastry M, Soto C, Stewart-Jones G B, Thomas P V, Van Galen J G, Baxa U, Lee K K, Mascola J R, Graham B S, Kwong P D. 2016. Iterative structure-based improvement of a fusion-glycoprotein vaccine against RSV. Nat Struct Mol Biol. 23:811-20.
12. Johnson T R, Rangel D, Graham B S, Brough D E, Gall J G.
Genetic vaccine for respiratory syncytial virus provides protection without disease potentiation.
Mol Ther. 2014 Jan; 22(1):196-205.
13. Johnson T R, Rao S, Seder R A, Chen M, Graham B S. 2009. TLR9 agonist, but not TLR7/8, functions as an adjuvant to diminish FI-RSV vaccine-enhanced disease, while either agonist used as therapy during primary RSV infection increases disease severity. Vaccine. 27:3045-52.
14. Kinnear E, Lambert L. McDonald J U, Cheeseman H M, Caproni L J, Tregoning J S, Airway T cells protect against RSV infection in the absence of antibody, Mucosal Immunol. 2017 May 24
15. Krarup A. Truan D. Furmanova-Hollenstein P, Bogaert L. Bouchier P, Bisschop I J, Widjojoatmodjo M N Zahn R. Schuitemaker H. McLellan J S, Langedijk J P. 2015. A highly stable prefusion RSV F vaccine derived from structural analysis of the fusion mechanism. Nat Commun. 6:8143.
16. Lu L, Palaniyandi S, Zeng R, Bai Y, Liu X, Wang Y, Pauza C D, Roopenian D C, Zhu X. 2011. An FcRn-targeted mucosal vaccine strategy effectively induces HIV-1 antigen-specific immunity to genital infection. J.Virol. 85:10542-10553.
17. Lycke N. 2012. Recent progress in mucosal vaccine development; potential and limitations. Nat Rev Immunol. 12:592-605.
18. McLellan J S, Chen M, Joyce M G, Sastry M, Stewart-Jones G B, Yang Y, Zhang B, Chen L, Srivatsan S, Zheng A, Zhou T, Graepel K W, Kumar A, Moin S, Boyington J C, Chuang G Y, Soto C, Baxa U, Bakker A Q, Spits H, Beaumont T, Zheng Z, Xia N, Ko S Y, Todd J P, Rao S, Graham B S, Kwong P D. 2013. Structure-based design of a fusion glycoprotein vaccine for respiratory syncytial virus. Science. 342:592-8.
19. McGhee J R, Mestecky J, Dertzbaugh M T, Eldridge J H, et al. 1992. The mucosal immune system: from fundamental concepts to vaccine development. Vaccine 10:75-88.
20. McGhee J R. 2011. A mucosal gateway for vaccines. Nat Biotechnol. 29:136-8.
21. McMaster S R, Wilson J J, Wang H, Kohlmeier J E. 2015. Airway-Resident Memory CD8 T Cells Provide Antigen-Specific Protection against Respiratory Virus Challenge through Rapid IFN-γ Production. J Immunol. 195:203-9.
22. Moghaddam A, Olszewska W, Wang B, Tregoning J S, Helson R, Sattentau Q J, Openshaw P J. 2006. A potential molecular mechanism for hypersensitivity caused by formalin-inactivated vaccines. Nat Med. 12:905-7.
23. Morabito K M, Ruckwardt T R, Redwood A J, Moin S M, Price D A, Graham B S. 2017. Intranasal administration of RSV antigen-expressing MCMV elicits robust tissue-resident effector and effector memory CD8+ T cells in the lung. Mucosal Immunol. 10:545-554;
24. Neutra M R, Kozlowski P A. 2006. Mucosal vaccines: the promise and the challenge. Nat Rev Immunol. 6:148-58.
25. Ngwuta J O, Chen M, Modjarrad K, Joyce M G, Kanekiyo M, Kumar A, Yassine H M, Moin S M, Killikelly A M, Chuang G Y, Druz A, Georgiev I S, Rundlet E J, Sastry M, Stewart-Jones G B, Yang Y, Zhang B. Nason M C, Capella C, Peeples M E, Ledgerwood J E, McLellan J S, Kwong P D, Graham B S. 2015. Prefusion F-specific antibodies determine the magnitude of RSV neutralizing activity in human sera. Sci Transl Med. 7:309ra162.
26. Openshaw P J, Tregoning J S. 2005. Immune responses and disease enhancement during respiratory syncytial virus infection. Clin Microbiol Rev. 18:541-55.
27. Oshansky C M, Zhang W, Moore E, Tripp R A. 2009. The host response and molecular pathogenesis associated with respiratory syncytial virus infection. Future Microbiol. 4:279-97.
28. Palomo C, Mas V, Thom M, Vázquez M, Cano O, Terrón M C, Luque D, Taylor G, Melero J A. 2016. Influence of Respiratory Syncytial Virus F Glycoprotein Conformation on Induction of Protective Immune Responses. J Virol. 90:5485-98.
29. Passmore C, Makidon P E, O'Konek J J, Zahn J A, Pannu J, et al. Intranasal immunization with W 80 5EC adjuvanted recombinant RSV rF-ptn enhances clearance of respiratory syncytial virus in a mouse model. Hum Vaccin Immunother. 2014; 10(3):615-22.
30. Pavot V, Rochereau N, Genin C, Verrier B, Paul S. 2012. New insights in mucosal vaccine development. Vaccine. 30:142-54.
31. Pierantoni A, Esposito M L, Ammendola V, Napolitano F, Grazioli F, et al. Mucosal delivery of a vectored RSV vaccine is safe and elicits protective immunity in rodents and nonhuman primates. Mol Ther Methods Clin Dev. 2015 May 20:2.15018.
32. Roopenian D C, Akilesh S. 2007. FcRn: the neonatal Fc receptor comes of age. Nat Rev Immunol. 7:715-25.
33. Rudd P A, Chen W, Mahalingam S. 2016. Mouse and Cotton Rat Models of human Respiratory Syncytial Virus. Methods Mol Biol. 1442:209-17.
34. Vissers M, Ahout I M L, de Jonge M I, Ferwerda G. 2016. Mucosal IgG levels correlate better with respiratory syncytial virus load and inflammation than plasma IgG levels. Clin Vaccine Immunol 23:243-245.
35. Welliver R C Sr. 2008. The immune response to respiratory syncytial virus infection: friend or foe? Clin Rev Allergy Immunol. 34:163-73.
36. Woodrow K A, Bennett K M, Lo D D. 2012. Mucosal vaccine design and delivery. Annu Rev Biomed Eng. 14:17-46.
37. Yang K, Varga S M. 2014. Mucosal vaccines against respiratory syncytial virus. Curr Opin Virol. 678-84.

38. Ye L, Zeng R, Bai Y, Roopenian D C, Zhu X. 2011. Efficient mucosal vaccination mediated by the neonatal Fc receptor. Nature Biotechnol. 29:158-163.
39. http://www.grandviewvresearch.com/press-release/lobal-vaccine-market
40. https:www.cdc.gov/features/rsv/
41. https://www.fiercepharma.com/vaccines/bavarian-nordic-reports-positve-rsv-vaccine-top-line-ohase-2-data.
42. https://www.fiereepharma.com/vaccines/novavasx-still-gunning-for-first-to-market-status-rsv-ceo
43. https://seekingalpha.com/article/4061495-novavax-will-ride-high-rsv-vaccine-wave-2017

We claim:

1. A trimeric protein comprising three peptides, wherein each of the three peptides comprise
   a monomeric Fc fragment of an immunoglobulin recognized by a neonatal receptor (FcRn), wherein the monomeric Fc fragment comprises an amino acid mutation that prevents dimer formation with other monomeric Fc fragments, wherein the monomeric Fc fragment of an immunoglobulin recognized by a FcRn comprises a mutation in the cysteine residues responsible for dimer formation;
   a modified pre-fusion respiratory syncytia virus (RSV) F protein; and
   a trimerization domain.

2. The trimeric protein of claim 1, wherein the monomeric Fc fragment of an immunoglobulin recognized by a FcRn is an IgG Fc fragment.

3. The trimeric protein of claim 1, wherein the trimerization domain is a T4 fibritin trimerization domain.

4. The trimeric protein of claim 3, wherein the T4 fibritin trimerization domain is foldon.

5. The trimeric protein of claim 1, wherein the monomeric Fc fragment of an immunoglobulin recognized by a FcRn is conjugated to the carboxy terminal end of the modified pre-fusion RSV F protein.

6. The trimeric protein of claim 1, wherein each of the peptides can further comprise one or more linkers.

7. The trimeric protein of claim 6, wherein at least one of the one or more linkers is on the N-terminus end of the monomeric Fc fragment of an immunoglobulin recognized by a FcRn.

8. The trimeric protein of claim 6, wherein at least one of the one or more linkers is on the C-terminus end of the monomeric Fc fragment of an immunoglobulin recognized by a FcRn.

9. The trimeric protein of claim 6, wherein the one or more linkers comprises a GS-linker.

10. The trimeric protein of claim 1, wherein the modified pre-fusion RSV F protein is mutated in the transmembrane domain.

11. The trimeric protein of claim 10, wherein the modified pre-fusion RSV F protein is further mutated in the cytoplasmic tail.

12. A composition comprising one or more of the trimeric proteins of claim 1.

13. The composition of claim 12, wherein the composition is a vaccine.

14. The composition of claim 12 further comprising a pharmaceutically acceptable carrier.

15. A method for eliciting a protective immune response against RSV comprising administering to a subject an effective amount of a composition comprising a trimeric protein comprising three peptides, wherein
   each of the three peptides comprises
   a monomeric Fc fragment of an immunoglobulin recognized by a neonatal
      receptor (FcRn), wherein the monomeric Fc fragment comprises an amino acid mutation that prevents dimer formation with other monomeric Fc fragments;
   a modified pre-fusion respiratory syncytia virus (RSV) F protein; and
   a trimerization domain, wherein the administering is to a mucosal epithelium.

16. The method of claim 15, wherein the trimerization domain is a T4 fibritin trimerization domain.

17. The method of claim 15, wherein the mucosal epithelium is selected from the group consisting of: lungs, intestines, trachea, colon, nasal tissue, and vaginal tissue.

18. The method of claim 15, wherein the administering is intranasal administering.

19. The method of claim 15, wherein an adjuvant is further administered with the composition.

20. The method of claim 19, wherein the adjuvant is CpG or MPL.

21. A method of treating a subject exposed to RSV or at risk of being exposed to RSV comprising administering to the subject an effective amount of a composition comprising a trimeric protein comprising three peptides wherein each of the three peptides comprises
   a monomeric Fc fragment of an immunoglobulin recognized by a neonatal
      receptor (FcRn), wherein the monomeric Fc fragment comprises an amino acid mutation that prevents dimer formation with other monomeric Fc fragments;
   a modified pre-fusion respiratory syncytia virus (RSV) F protein; and
   a trimerization domain, wherein the administering is to a mucosal epithelium.

22. The method of claim 21, wherein the administering is intranasal administering.

23. The trimer protein of claim 1, wherein the three peptides are trimerized via the trimerization domain.

* * * * *